(12) United States Patent
Kamiyama

(10) Patent No.: US 7,744,533 B2
(45) Date of Patent: Jun. 29, 2010

(54) ULTRASONIC DIAGNOSTIC APPARATUS, IMAGE PROCESSING APPARATUS AND IMAGE PROCESSING METHOD

(75) Inventor: Naohisa Kamiyama, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 827 days.

(21) Appl. No.: 11/174,728

(22) Filed: Jul. 6, 2005

(65) Prior Publication Data

US 2006/0020205 A1    Jan. 26, 2006

(30) Foreign Application Priority Data

Jul. 7, 2004    (JP) ............... 2004-201040

(51) Int. Cl.
*A61B 8/00* (2006.01)
(52) U.S. Cl. ...................... 600/437; 600/407
(58) Field of Classification Search ......... 600/443–445, 600/449, 459; 601/2–4; 604/19, 20
See application file for complete search history.

(56) References Cited

U.S. PATENT DOCUMENTS

| | | | |
|---|---|---|---|
| 5,694,937 A | 12/1997 | Kamiyama | |
| 5,743,266 A | 4/1998 | Levene et al. | |
| 5,797,397 A | 8/1998 | Rosenberg | |
| 2002/0103437 A1* | 8/2002 | Jibiki | 600/454 |
| 2004/0215076 A1 | 10/2004 | Kamiyama | |
| 2005/0049500 A1* | 3/2005 | Babu et al. | 600/443 |
| 2005/0059893 A1 | 3/2005 | Ogasawara et al. | |

FOREIGN PATENT DOCUMENTS

| | | |
|---|---|---|
| JP | 8-7074 | 1/1996 |
| JP | 2002-238901 | 8/2002 |

* cited by examiner

*Primary Examiner*—Long V Le
*Assistant Examiner*—Saurel J Selkin
(74) *Attorney, Agent, or Firm*—Oblon, Spivak, McClelland, Maier & Neustadt, L.L.P.

(57) ABSTRACT

An ultrasonic diagnostic apparatus comprises a unit for generating image data, an image reconstructing unit and an image synthesizing unit. The unit for generating image data generates image data for displaying a tomogram of a subject by luminance according to signal intensities of echo signals obtained through ultrasonic waves transmitted to the subject. The image reconstructing unit generates reconstructed images by alternating at least one of a luminance and a color of an area of a predetermined luminance so that the area of the predetermined luminance is emphasized in the image data while the predetermined luminance is altered in turn. The image synthesizing unit supplies the reconstructed images to a display unit so that the reconstructed images are displayed on the display unit in turn.

22 Claims, 12 Drawing Sheets

ULTRASONIC DIAGNOSTIC APPARATUS, IMAGE PROCESSING APPARATUS AND IMAGE PROCESSING METHOD

BACKGROUND OF THE INVENTION

1. Field of the Invention

The present invention relates to an ultrasonic diagnostic apparatus, an image processing apparatus and an image processing method which image a tomogram of a subject according to echo signals of an ultrasonic wave irradiated to the subject, and more particularly, to an ultrasonic diagnostic apparatus, an image processing apparatus and an image processing method, which have a function for image processing to improve contrast visibility of tomograms.

2. Description of the Related Art

An ultrasonic diagnosis is a diagnosis in which heart beat or motions of a fetus can be obtained as a real-time display through a manipulation as simple as placing an ultrasonic probe to the body surface. Furthermore, an ultrasonic diagnosis has no exposure risk different from X-ray imaging or the like. Therefore, in an ultrasonic diagnosis, an examination can be performed repetitively due to its high safety. The foregoing advantages enable the use of an ultrasonic diagnosis in the obstetrics department, home medical care, etc.

Moreover, an ultrasonic diagnosis apparatus can be moved to a bedside, so that an examination can be readily performed at the bedside, owing to its small system size in comparison with other image diagnosis apparatus for X-ray CT (computed tomography) apparatus, MRI (magnetic resonance imaging) apparatus, etc. Although the ultrasonic diagnostic apparatus varies with kinds of functions furnished therewith, the one small enough for an individual to carry around with one hand has been developed.

An intravenous ultrasound contrast medium has been commercialized, and the contrast echo method is thus being performed in recent years. This method aims to evaluate a blood perfusion when examining, for example, the heart or liver by enhancing blood flow signals with the aid of an ultrasound contrast medium injected intravenously. In most of the contrast media, micro bubbles function as the reflection source.

In an above mentioned examination using an ultrasound contrast medium, a very detailed blood vessel structure can be imaged, compared with the ultrasonic Doppler method used as conventional technology. It is expected that blood flow information at the level obtained by this contrast echo method is to be information of great importance for a differential diagnosis such as the degree of progress of the shunt of vessels or regenerative nodules and the differential diagnosis of a diffuse liver disease or a liver cancer.

The basic use of the ultrasonic diagnosis is to observe the morphology and movement of an internal organ from acquired tomographic images. Another important use thereof is to mutually compare the degrees of luminance (contrast ratios of luminance) expressed in the tomographic image, and acquire diagnostic information therefrom. These methods for ultrasonic diagnosis are used not only in ordinary diagnosis in the B mode but also in the recent contrast echo methods, and the observation of tomographic images and the comparison between contrast ratios of luminance are becoming increasingly important elements of diagnosis.

For example, when a tomographic image is diagnosed by the comparison between contrast ratios of luminance, if the intensity of echo signals enhanced by a contrast medium is compared between a disease region such as tumor and a normal parenchyma region, the magnitude relationship between the blood volumes supplied to the respective regions can be known, so that the degree of malignancy of the target area can be diagnosed from the magnitude relationship between these blood volumes.

In another example, in a moving image varying with time, by grasping the temporal variation in the luminance of the tumor region, it is possible to know the characteristics of blood flows flowing into or out of the tumor region, and identify the disease based on a pattern of temporal variation of the luminance.

Regarding above-mentioned ultrasonic diagnosis apparatus, as well as an image diagnostic apparatus such as an X-ray CT apparatus, MRI, and the like, the visibility of a tomographic image during diagnosis constitutes an important element common thereto, and hence, a technique for improving the visibility of tomographic image has been proposed (see, for example, JP-A-H8-7074). This technique divides a tomographic image of X-ray CT image or the like into a background section and a region of interest based on the difference in the pixel value, and allocates luminance gradation of a low luminance to the background section while allocating luminance gradation of a high luminance to the region of interest, whereby the region of interest and the background section can be definitely distinguished from each other. Furthermore, this technique is devised so that a pixel value that is referred to as a threshold value when the region of interest and the background section are divided from each other, can be altered.

In the ultrasonic diagnostic apparatus, as described above, the improvement in the contrast ratio of luminance is an important challenge. To improve the contrast ratio of luminance, it is necessary to enhance basic performance such as an S/N ratio of the apparatus. However, besides such basic performance of the apparatus, illusion (so-called "optical illusion") brought about by human feeling may constitute a problem with respect to the contrast ratio of luminance.

FIG. 18 is a real image which explains an example case optical illusion is to be a problem on diagnosis of a luminance contrast ratio. FIG. 19 is an illustration image which explains an example case optical illusion is to be a problem on diagnosis of a luminance contrast ratio.

FIGS. 18 and 19 are schematic views each showing a diagnostic image with the region R of interest vertically oriented in the center of the screen. In FIGS. 18 and 19, the region R of interest has a single luminance, but the background B is varied in the luminance depending on a location. As a result, under the influence of the luminance of the background B, the luminance level of the region R of interest is felt as being different at different locations, and in this case of FIGS. 18 and 19, it is felt as being different along the vertical direction. Such a phenomenon that a luminance level is felt to be one different from the actual luminance level thereof is attributable to human optical illusion.

Moving images are also subjected to influence of the optical illusion as in the case of static images. For example, provided the luminance level of the region of interest is constant in time, when the luminance of the background around the region of interest gradually changes toward the higher luminance side, the luminance of the region of interest looks as if it were changing toward the lower luminance side.

The occurrence of such an illusion may cause a risk that diagnostic information is not properly recognized, which can result in a misdiagnosis. The optical illusion, therefore, must be avoided to prevent a misdiagnosis.

However, the conventional visibility improving techniques have been directed to merely altering luminances of the region of interest and background, and no consideration has been given to optical illusion. Therefore, no countermeasures to avoid the optical illusion have been taken. As a result, as described above, in the case where the luminance of the background varies with time, or varies depending on a location, the optical illusion may still occur and incur a misdiagnosis.

On the other hand, as a conventional solution to the optical illusion, a method has been contemplated in which the luminance level of the region of interest is digitalized, histogram-displayed, or graph-displayed, and in which the luminance level subjected to the digitalization, histogram-displaying, or graph-displaying is referred to during diagnosis.

However, this method for digitalizing or graphing the luminance level makes it difficult to observe the overall diagnostic images. Also, because the histograms use values such as the averaged values and the like with respect to the region of interest, they do not suit to the case where minute changes closely associated with the diagnostic images are observed.

SUMMARY OF THE INVENTION

Accordingly, the present invention has been made in light of the conventional situations, and it is an objective of the present invention to provide an ultrasonic diagnostic apparatus, an image processing apparatus and an image processing method which have a function for image processing making it possible to improve visibility for contrast of luminance on a diagnostic image by reducing the influence of optical illusion.

In an aspect, to achieve the objective, the present invention provides an ultrasonic diagnostic apparatus comprising a unit for generating image data for displaying a tomogram of a subject by luminance according to signal intensities of echo signals obtained through ultrasonic waves transmitted to the subject; an image reconstructing unit for generating reconstructed images by alternating at least one of a luminance and a color of an area of a predetermined luminance so that the area of the predetermined luminance is emphasized in the image data while the predetermined luminance is altered in turn; and an image synthesizing unit for supplying the reconstructed images to a display unit so that the reconstructed images are displayed on the display unit in turn.

Furthermore, in an aspect, to achieve the objective, the present invention provides an ultrasonic diagnostic apparatus comprising a unit for generating image data for displaying a tomogram of a subject by luminance according to signal intensities of echo signals obtained through ultrasonic waves transmitted to the subject; an image generating unit for generating processed images by performing different processings to the image data; and an image synthesizing unit for performing an image synthesizing processing so that the processed images super-positioned are displayed by luminance using respectively different colors.

Furthermore, in an aspect, to achieve the objective, the present invention provides an ultrasonic diagnostic apparatus comprising a unit for generating image data for displaying a tomogram of a subject by luminance according to signal intensities of echo signals obtained through ultrasonic waves transmitted to the subject; a luminance scale altering unit for generating new luminance scales by altering at least ones of colors and color tones corresponding partial luminance levels of luminance scale with which the image data are to be displayed by the luminance, the partial luminance levels being different each other; an image reconstructing unit for performing an image reconstruction processing to the image data according to the new luminance scales respectively to generate a plurality of new image data; a coloring condition setting unit for setting times for displaying the plurality of new image data as a display time information and an order for displaying the plurality of new image data as an display order information; and an image synthesizing unit for giving the plurality of new image data to a display unit so that the plurality of new image data are displayed in a display order designated by the display order information during display times designated by the display time information on the display unit.

Furthermore, in an aspect, to achieve the objective, the present invention provides an ultrasonic diagnostic apparatus comprising a unit for generating a plurality of image data in a time series for displaying tomograms of a subject by luminance according to signal intensities of echo signals obtained through ultrasonic waves transmitted to the subject at least two times, the tomograms corresponding to a plurality of frames; an image generating unit for performing a maximum luminance level holding operation which is an operation for holding a luminance level at a corresponding position spatially of the plurality of image data to a maximum so as to generate a plurality of new image data; a first color tone altering unit for performing an image reconstruction processing which alters a color tone of the plurality of new image data to a first color tone predetermined; a second color tone altering unit for performing another image reconstruction processing which alters a color tone of the plurality of image data without the maximum luminance level holding operation to a second color tone predetermined; and an image synthesizing unit for giving image data having the first color tone altered and image data having the second color tone altered to a display unit so that they are super positioned to be display on the display unit.

Furthermore, in an aspect, to achieve the objective, the present invention provides an ultrasonic diagnostic apparatus comprising a unit for generating a plurality of image data in a time series for displaying tomograms of a subject by luminance according to signal intensities of echo signals obtained through ultrasonic waves transmitted to the subject at least two times, the tomograms corresponding to a plurality of frames; a timing setting unit for generating a time information according to an information designating a timing input from an input device; a first color tone altering unit for performing an image reconstruction processing which alters a color tone of specific image data included in the plurality of image data to a first color tone predetermined, the specific image data corresponding on a time designated by the time information; a second color tone altering unit for performing another image reconstruction processing which alters a color tone of at least two image data included in the plurality of image data to a second color tone predetermined, the two image data corresponding after the time designated by the time information; and an image synthesizing unit for giving image data having the first color tone altered and image data having the second color tone altered to a display unit so that they are super positioned to be display on the display unit.

Furthermore, in an aspect, to achieve the objective, the present invention provides an ultrasonic diagnostic apparatus comprising a unit for generating image data for displaying a tomogram of a subject by luminance according to signal intensities of echo signals obtained through ultrasonic waves transmitted to the subject; a luminance scale altering unit for generating new luminance scale by altering at least ones of colors and color tones corresponding partial luminance levels of a background color in luminance scale with which the image data are to be displayed by the luminance to at least ones of other colors and other color tones reducing an influence of an optical illusion; an image reconstructing unit for performing an image reconstruction processing to the image data according to the new luminance scale to generate new image data; and an image synthesizing unit for giving the new image data to a display unit so that the new image data are to be display on the display unit.

Furthermore, in an aspect, to achieve the objective, the present invention provides an image processing apparatus comprising an image reconstructing unit for generating reconstructed images by alternating at least one of a luminance and a color of an area of a predetermined luminance in image data generated for displaying a tomogram of a subject by luminance so that the area of the predetermined luminance is emphasized in the image data while the predetermined luminance is altered in turn; and an image synthesizing unit for supplying the reconstructed images to a display unit so that the reconstructed images are displayed on the display unit in turn.

Furthermore, in an aspect, to achieve the objective, the present invention provides an image processing apparatus comprising an image generating unit for generating processed images by performing different processings to image data generated for displaying a tomogram of a subject by luminance; and an image synthesizing unit for performing an image synthesizing processing so that the processed images super-positioned are displayed by luminance using respectively different colors.

Furthermore, in an aspect, to achieve the objective, the present invention provides an image processing apparatus comprising a luminance scale altering unit for generating new luminance scales by altering at least ones of colors and color tones corresponding partial luminance levels of luminance scale with which image generated for displaying a tomogram of a subject by luminance data are to be displayed by the luminance, the partial luminance levels being different each other; an image reconstructing unit for performing an image reconstruction processing to the image data according to the new luminance scales respectively to generate a plurality of new image data; and a coloring condition setting unit for setting times for displaying the plurality of new image data as a display time information and an order for displaying the plurality of new image data as an display order information.

Furthermore, in an aspect, to achieve the objective, the present invention provides an image processing apparatus comprising an image generating unit for performing a maximum luminance level holding operation which is an operation for holding a luminance level at a corresponding position spatially of plurality of image data generated in a time series for displaying tomograms of a subject by luminance to a maximum so as to generate a plurality of new image data, the tomograms corresponding to a plurality of frames; a first color tone altering unit for performing an image reconstruction processing which alters a color tone of the plurality of new image data to a first color tone predetermined; a second color tone altering unit for performing another image reconstruction processing which alters a color tone of the plurality of image data without the maximum luminance level holding operation to a second color tone predetermined; and an image synthesizing unit for giving image data having the first color tone altered and image data having the second color tone altered to a display unit so that they are super positioned to be display on the display unit.

Furthermore, in an aspect, to achieve the objective, the present invention provides an image processing apparatus comprising a timing setting unit for generating a time information according to an information designating a timing input from an input device; a first color tone altering unit for performing an image reconstruction processing which alters a color tone of specific image data included in a plurality of image data generated in a time series for displaying tomograms corresponding to frames of a subject by luminance to a first color tone predetermined, the specific image data corresponding on a time designated by the time information; a second color tone altering unit for performing another image reconstruction processing which alters a color tone of at least two image data included in the plurality of image data to a second color tone predetermined, the two image data corresponding after the time designated by the time information; and an image synthesizing unit for giving image data having the first color tone altered and image data having the second color tone altered to a display unit so that they are super positioned to be display on the display unit.

Furthermore, in an aspect, to achieve the objective, the present invention provides an image processing apparatus comprising a luminance scale altering unit for generating new luminance scale by altering at least ones of colors and color tones corresponding partial luminance levels of a background color in luminance scale with which image data generated for displaying a tomogram of a subject by luminance are to be displayed by the luminance to at least ones of other colors and other color tones reducing an influence of an optical illusion; and an image reconstructing unit for performing an image reconstruction processing to the image data according to the new luminance scale to generate new image data.

Furthermore, in an aspect, to achieve the objective, the present invention provides an image processing method comprising steps of: generating reconstructed images by alternating at least one of a luminance and a color of an area of a predetermined luminance in image data generated for displaying a tomogram of a subject by luminance so that the area of the predetermined luminance is emphasized in the image data while the predetermined luminance is altered in turn; and supplying the reconstructed images to a display unit so that the reconstructed images are displayed on the display unit in turn.

Furthermore, in an aspect, to achieve the objective, the present invention provides an image processing method comprising steps of: generating processed images by performing different processings to image data generated for displaying a tomogram of a subject by luminance; and performing an image synthesizing processing so that the processed images super-positioned are displayed by luminance using respectively different colors.

Furthermore, in an aspect, to achieve the objective, the present invention provides an image processing method comprising steps of: generating new luminance scales by altering at least ones of colors and color tones corresponding partial luminance levels of luminance scale with which image generated for displaying a tomogram of a subject by luminance data are to be displayed by the luminance, the partial luminance levels being different each other; performing an image reconstruction processing to the image data according to the new luminance scales respectively to generate a plurality of new image data; and setting times for displaying the plurality of new image data as a display time information and an order for displaying the plurality of new image data as an display order information.

Furthermore, in an aspect, to achieve the objective, the present invention provides an image processing method comprising steps of: performing a maximum luminance level holding operation which is an operation for holding a luminance level at a corresponding position spatially of plurality of image data generated in a time series for displaying tomograms of a subject by luminance to a maximum so as to generate a plurality of new image data, the tomograms corresponding to a plurality of frames; performing an image reconstruction processing which alters a color tone of the plurality of new image data to a first color tone predetermined; performing another image reconstruction processing which alters a color tone of the plurality of image data without the maximum luminance level holding operation to a second color tone predetermined; and giving image data having the first color tone altered and image data having the second color tone altered to a display unit so that they are super positioned to be display on the display unit.

Furthermore, in an aspect, to achieve the objective, the present invention provides an image processing method comprising steps of: generating a time information according to an information designating a timing input from an input device; performing an image reconstruction processing which alters a color tone of specific image data included in a plurality of image data generated in a time series for displaying tomograms corresponding to frames of a subject by luminance to a first color tone predetermined, the specific image data corresponding on a time designated by the time information; performing another image reconstruction processing which alters a color tone of at least two image data included in the plurality of image data to a second color tone predetermined, the two image data corresponding after the time designated by the time information; and giving image data having the first color tone altered and image data having the second color tone altered to a display unit so that they are super positioned to be display on the display unit.

Furthermore, in an aspect, to achieve the objective, the present invention provides an image processing method comprising steps of: generating new luminance scale by altering at least ones of colors and color tones corresponding partial luminance levels of a background color in luminance scale with which image data generated for displaying a tomogram of a subject by luminance are to be displayed by the luminance to at least ones of other colors and other color tones reducing an influence of an optical illusion; and performing an image reconstruction processing to the image data according to the new luminance scale to generate new image data.

With the ultrasonic diagnostic apparatus, the image processing apparatus and the image processing method as described above, it is possible to improve visibility for contrast of luminance on a diagnostic image by reducing the influence of optical illusion.

DESCRIPTION OF THE PREFERRED EMBODIMENTS

An ultrasonic diagnostic apparatus, an image processing apparatus and an image processing method according to embodiments of the present invention will be described with reference to the accompanying drawings.

Figure 1:
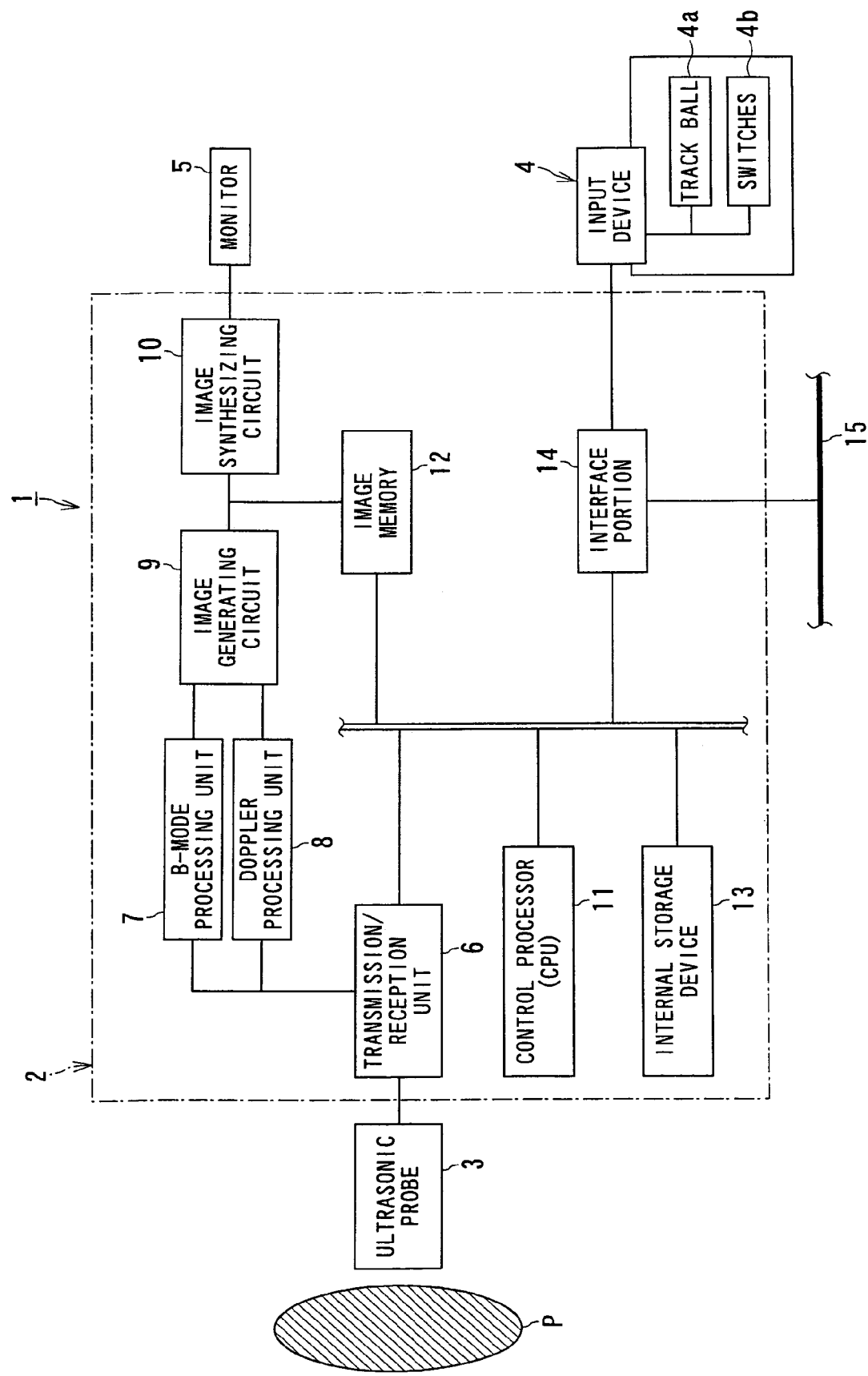
FIG. 1 is a block diagram showing an ultrasonic diagnostic apparatus according to a first embodiment of the present invention.

FIG. 1 is a block diagram showing an ultrasonic diagnostic apparatus according to a first embodiment of the present invention.

The ultrasonic diagnostic apparatus 1 includes an ultrasonic probe 3, an input device 4 and a monitor 5 as a display unit connected to an apparatus main body 2. The apparatus main body 2 includes a transmission/reception unit 6, a B-mode processing unit 7, a Doppler processing unit 8, an image generating circuit 9, an image synthesizing circuit 10, a control processor 11, an image memory 12, an internal storage device 13 and an interface portion 14. The ultrasonic transmission/reception unit 6 and the like built into the apparatus main body 2 may be in the form of hardware, such as integrated circuits, or they may be in the form of softwarily modularized software programs. The following description will describe functions of the components individually.

The ultrasonic probe 3 includes plural piezoelectric transducers that generate ultrasonic waves to transmit to a subject P according to a driving signal from the ultrasonic transmission/reception unit 6 and receive reflection waves from the subject P to convert to electrical signals; matching layers provided to the piezoelectric transducers; backing materials used to prevent backward propagation of ultrasonic waves from the piezoelectric transducers, etc.

When an ultrasonic wave is transmitted to the subject P from the ultrasonic probe 3, the transmitted ultrasonic wave reflects consecutively on the discontinuous surfaces of acoustic impedance in tissues of the body, and reflections are received at the ultrasonic probe 3 as echo signals. The amplitude of the echo signals depends on a difference in acoustic impedance between the discontinuous surfaces on which reflection of the ultrasonic wave takes place. In a case where transmitted ultrasonic pulses are reflected on the surface of a blood flow, the heart wall or the like in motion, the echoes undergo frequency deviation by the Doppler effect, depending on the velocity components of the moving substance in the ultrasonic transmission direction.

The input device 4 is connected to the apparatus main body 2, and includes a track ball 4a and various switches 4b through which the operator inputs all sorts of information such as various instructions, conditions, setting instructions of the region of interest (ROI), setting instructions of various image quality conditions, etc. into the apparatus main body 2.

The monitor 14 has a function to display the morphologic information and blood flow information in the living body in the form of images according to video signals from the image synthesizing circuit 10.

The transmission/reception unit 6 includes a trigger generating circuit, a delay circuit, a pulsar circuit, etc. (all of which are not shown in the drawing) which are normally included as components on the side of the ultrasonic transmission. The pulsar circuit has a function to generate a rate pulse used to generate an ultrasonic wave to be transmitted repetitively, at a predetermined rate frequency, fr Hz (period: 1/fr sec.) The generated rate pulse is supplied to the delay circuit. The delay circuit has a function to give each rate pulse, which is given from the pulsar circuit, a delay time needed to focus an ultrasonic wave to a beam shape and determine the transmission directivity for each channel. The rate pulse with the delay time is supplied form the delay circuit to the trigger generating circuit. The trigger generating circuit has a function to impress a driving pulse to the ultrasonic probe 3 at the timing based on the resulting rate pulse supplied from the delay circuit.

In order to perform a scan sequence, the transmission/reception unit 6 is furnished with a function of changing instantaneously a transmission condition of ultrasonic waves, such as a transmission frequency, a transmission driving voltage, at a control signal from the control processor 11. In particularly, the transmission driving voltage can be changed by a linear amplifier type oscillation circuit capable of switching its value instantaneously or a mechanism that electrically switches plural power supply units.

In addition, the transmission/reception unit 6 includes an amplifier circuit, an analog-to-digital (A/D) converter, an adder, etc. (all of which are not shown in the drawing) which are normally included as components on the side of the ultrasonic reception. The amplifier circuit has a function to amplify an echo signal captured via the ultrasonic probe 3 for each channel and a function to give the amplified echo signal to the analog-to-digital converter. The analog-to-digital converter has a function to give the echo signal amplified by the amplifier circuit a delay time needed to determine the reception directivity and to give the result echo signal to the adder. The adder has a function to perform addition processing to the echo signals given from the analog-to-digital converter.

This addition of the echo signals by the adder enhances the reflection components of the echo signals in a direction corresponding to the reception directivity, and the reception directivity and the transmission directivity together form an integrated beam for ultrasonic transmission and reception.

The B-mode processing unit 7 has a function to receive an echo signal from the transmission/reception unit 6 and perform various processings, such as a receiving filter process so as to make a signal to noise ratio (SNR) optimal to extract a signal needed for a diagnostic image. In addition, the tissue harmonic imaging method which extracts a twice-harmonic component to a transmitted ultrasonic wave for imaging is adopted in recent years. This extracting of the harmonic signal is also performed in the B mode-processing unit 7. Furthermore, the B mode-processing unit 7 has a function to perform a process such as logarithmic amplification processing, envelope detection processing, etc. on the extracted signal after extracting a signal needed for a diagnostic image to generate data of which signal intensity can be represented by the luminance, in other word, which can be displayed by luminance.

The Doppler processing unit 8 has a function to perform frequency analysis to obtain the velocity information from the echo signal received from the transmission/reception unit 6 and extract a blood flow, tissues, and contrast medium echo components due to the Doppler effect from the echo signal to find blood flow information, such as the average velocity, dispersion, and power, at a number of points.

The information generated in the B mode-processing unit 7 is given to the image generating circuit 9 as B-mode image information. The information generated in the Doppler processing unit 8 is given to the image generating circuit 9 as Doppler image information. The image generating circuit 9 has a function to generate an image depend on a user's request by bearing a role of the so-called post processor which performs a image processing such as time smoothing processing including addition average processing of two or more images, edge extraction processing including spatial differentiation processing, and so on. With regard to Doppler images, the image generating circuit 9 generates an average velocity image, a dispersion image, or a power image, either solely or in combination.

The control processor 11 functions as an information-processing unit (computer), and also is a control unit which controls the operations of the apparatus main body 2 by performing various programs.

The image memory 12 comprises a storage memory used to store image data, which is corresponding to image information generated in the image generating circuit 9, received from the image generating circuit 9. The image data stored in the image memory 12 is subject to an image reconstruction processing by the control processor 11 operating an image-processing program, according to need. The reconstructed image data after the image reconstruction processing can be given form the image memory 12 to the image synthesizing circuit 10 according to an operation of the input device 4 by user, for example, after a diagnosis.

The image data readout from the image memory 12 and output of the image generating circuit 9 are given to the image synthesizing circuit 10. The image synthesizing circuit 10 has a function to convert a sequence of scanning line signals of ultrasonic scans to a sequence of scanning line signals of a general video format typically used in TV sets or the like, and thereby generate an ultrasonic diagnostic image as a display image. Furthermore, the ultrasonic diagnostic image generated in the image synthesizing circuit 10 is synthesized with information such as values of parameter needed to a diagnosis, time information, a name of patient and so on to display on the monitor 5. Then, image data such as tomogram showing tissue shape of the subject P after performing the image reconstruction processing can be reproduce with information, such as a numerical value of a parameter on the monitor 5 in still image or in moving image using two or more two dimension-image data.

The interface portion 14 is an interface for transmitting and receiving information between the apparatus main body 2 and arbitrary one of the input device 4, the network 15 and a new external storage device (not shown).

The internal storage device 13 saves various information need to the ultrasonic scanning such as a scan sequence, control programs and image processing programs to perform various operation and processing including an image reconstruction processing, diagnostic information including IDs of patients and observations of doctors, diagnostic protocols, conditions of transmission and reception of ultrasonic waves and so on. The internal storage device 13 is also used to save image data in the image memory 12 when necessity arises. Various data in the internal storage device 13 can be transferred to a peripheral apparatus (not shown) via the interface circuit 29 and the network 15.

With each component of the above-dimensioned ultrasonic diagnostic apparatus 1, such as the ultrasonic probe 3, the transmission/reception unit 6, the control processor 11, various control programs stored in the internal storage device 13, the B-mode processing unit 7 or the Doppler processing unit 8, the image generating circuit 9, the ultrasonic diagnostic apparatus 1 functions as a unit generating image data for displaying a tomogram of the subject P by luminance according to intensity of echo signals obtained through transmitting ultrasonic waves to the subject P.

An image processing apparatus is built by the control processor 11 of the ultrasonic diagnostic apparatus 1 which reads the image processing program stored in the internal storage device 13.

Figure 2:
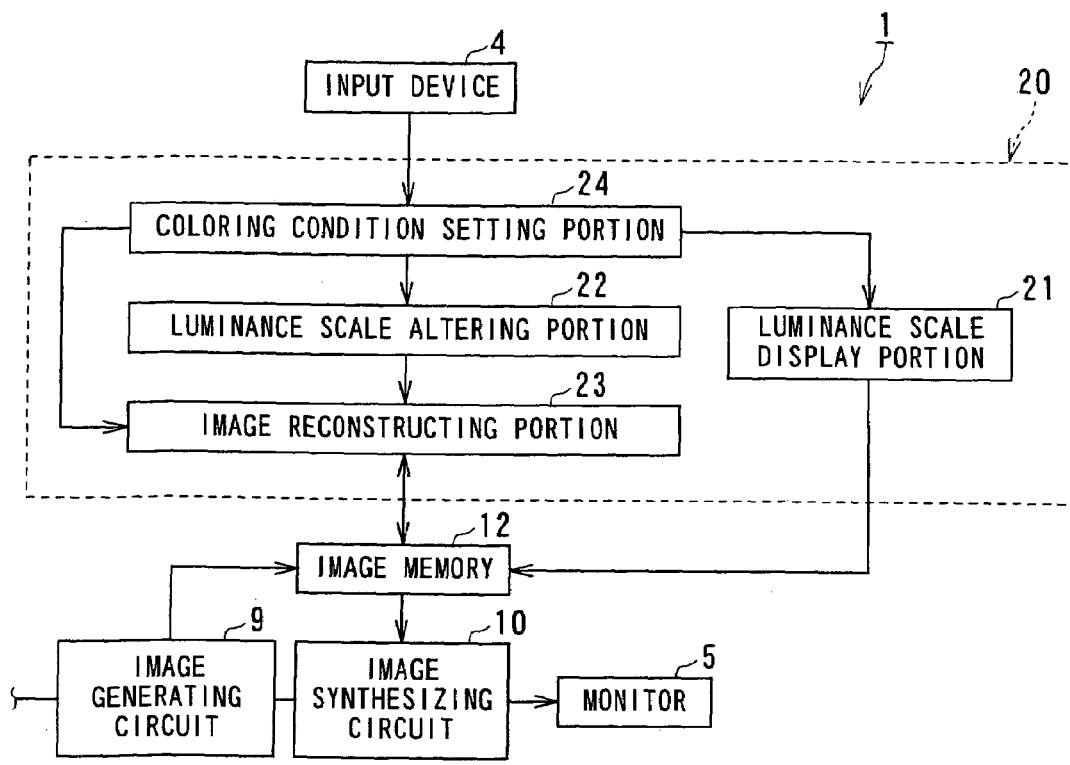
FIG. 2 is a functional block diagram showing construction of the image processing apparatus built in the apparatus main body of the ultrasonic diagnostic apparatus shown in FIG. 1.

FIG. 2 is a functional block diagram showing construction of the image processing apparatus built in the apparatus main body 2 of the ultrasonic diagnostic apparatus 1 shown in FIG. 1.

The image processing apparatus 20 includes a luminance scale display portion 21, a luminance scale altering portion 22, an image reconstructing portion 23 and a coloring condition setting portion 24.

The image processing device 20 has the functions of: altering a display color of regions, of luminance-displayable image data, that have the same luminance level or luminance levels within a definite range, into predesignated altered color to thereby display the altered display color for a designated time period; and performing image processing so that the regions of which the display color is altered change after the designated time has elapsed.

The luminance scale display portion 21 has the function of: when causing the monitor 5 to luminance-display image data stored in the image memory 12, generating luminance scale information for causing the monitor 5 to display an image representing the luminance scale separately, and writing it into the image memory 12.

The luminance scale altering portion 22 has the function of: altering a color and/or color tone corresponding to some luminance level in the luminance scale used when causing the monitor 5 to display the image data stored in the image memory 12 by the luminance, into a color and/or color tone that has been predesignated. That is, the luminance scale altering portion 22 has the function of altering a display color at some luminance level of the luminance scale into an altered color predesignated. The alteration range of the color and color tone of the luminance scale may be a color and color tone each at a single luminance level, or alternatively, a color and color tone each at any luminance level within a required range. Furthermore, a color and color tone each at a plurality of luminance levels can also be altered.

Also, the luminance scale altering portion 22 returns the display color at the luminance level at which the display color has already been altered into the altered color, to the original color while the display color corresponding to a luminance level that is another portion of the luminance scale is altered into the altered color so as to repetitively generate new luminance scales in turn so that the luminance level at which the display color is to be altered into an altered color varies with time. Here, when generating a luminance scale, display order information received from the coloring condition setting portion 24 is referred to.

The image reconstructing portion 23 has the functions of: reading image data stored in the image memory 12, sequentially reconstructing the image data so as to be displayed on the monitor 5 in accordance with the luminance scales generated by the luminance scale altering portion 22 for the time period designated by display time information received from the coloring condition setting portion 24, and in the order in accordance with display order information received from the coloring condition setting portion 24; and writing the image data acquired by the reconstruction into the image memory 12. Thus, the image reconstruction processing operation of the image reconstructing portion 23 makes it possible that the display color of regions having a specified luminance level in the image data stored in the image memory 12 is altered into a required altered color at a required order, and that it is displayed by the monitor 5 for a required time period.

The image reconstructing portion 23 further has the function of receiving display time information for designating the time for displaying the image data acquired by reconstruction and the display order information for designating the display order of image data of which the display color has been altered, from the coloring condition setting portion 24, and write them into the image memory 12 so as to be appended to the image data.

The coloring condition setting portion 24 has the functions of setting, as parameters in accordance with information received from the input device 4, display methods for image data that include: an altered color (color and/or color tone) used as a display color of regions having the same luminance level or luminance levels within a definite range, a display time when the regions having the same luminance level or luminance levels within a definite range are displayed in the altered color, the display order of the regions to be displayed in the altered color, and other necessary conditions for displaying the image data in the altered color. The coloring condition setting portion 24 further has the function of giving parameters, such as the altered color, display time, display order each of which has been set, to the luminance scale display portion 21, the luminance scale altering portion 22, and the image reconstructing portion 23. In addition, as required, the coloring condition setting portion 24 has the function of causing a setting screen for the parameters to be displayed, by generating screen information for setting parameters designating a display method for image data and writing it into the image memory 12.

The image synthesizing circuit 10 has the function of causing the monitor 14 to display the image data generated as described above and stored in the image memory 12, by repetitively giving the image data to the monitor 14 in turn for the time period according to the display time information, and in the order according to the display order information.

Next, the operation of the ultrasonic diagnostic apparatus 1 will be described.

Figure 3:
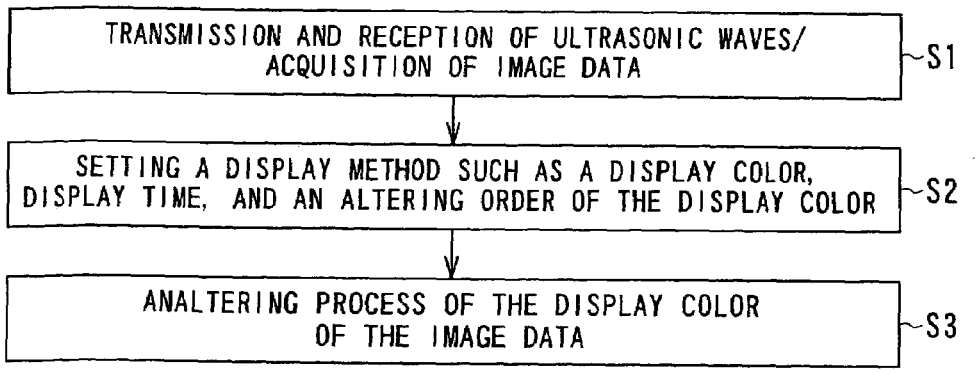
FIG. 3 is a flowchart showing a flow for indicating a diagnostic image by the ultrasonic diagnostic apparatus shown in FIG. 1.

FIG. 3 is a flowchart showing a flow for indicating a diagnostic image by the ultrasonic diagnostic apparatus 1 shown in FIG. 1. The symbols including S with a number in FIG. 3 indicate each step of the flowchart.

First, in the step S1, once ultrasonic waves have transmitted to, and received from a subject P, echo signals are acquired, and a tomographic image of the subject P is generated from the echo signals. Specifically, at timings based on a plurality of rate pulses generated each with a delay time in the transmission/reception unit 6, drive pulses are applied to respective piezoelectric transducers of the ultrasonic probe 3. As a result, ultrasonic waves are transmitted from the respective piezoelectric transducers of the probes 3 to the subject P. The ultrasonic waves transmitted to the subject P are reflected on impedance discontinuous surfaces of acoustic impedance in internal tissues and echo signals having amplitudes depending on the difference in the acoustic impedance on the discontinuous surfaces on which the ultrasonic waves were reflected are received by the ultrasonic probe 3.

The echo signals received by the ultrasonic probe 3 are amplified by an amplifier circuit in the transmission/reception unit 6. The amplified echo signals are converted into digital signals with a required delay time given in an A/D converter. Furthermore, the digitalized echo signals are subjected to addition processing in an adder, and then provided to the B-mode processing unit 7.

Next, in the B-mode processing unit 7, various processings of a reception filter and the like with respect to echo signals, and extraction processing with respect to signals used for diagnostic images are performed. Furthermore, processings such as logarithmic amplification processing, and envelope detection processing are performed to the extracted signals obtained by the extraction processing. Also, in the B-mode processing unit 7, data that can express the signal intensity of echo signals by the luminances is generated as B mode image information, and stored into the image memory 12.

On the other hand, as required, in the Doppler processing unit 8, frequency analysis of echo signals are performed, and information such as speed information on blood flows is acquired. Moreover, blood flow information, such as the average speed, dispersion, and power of blood flows, tissues and an echo component on a contrast medium under the Doppler effect are determined with respect to multiple points. The information such as blood flows and the like acquired in the Doppler processing unit 8 is stored in the image memory 12 as Doppler image information.

The B mode image information stored in the image memory 12 can be expressed by luminances of gray scale. For example, the B mode image can be expressed by a luminance of 64 gradation. However, when the B mode image is displayed on the monitor 5 using a luminance of 64 gradation gray scale, it may occur that the luminance of the region of interest is constant while the luminance of the background is different depending on a location. In this case, the luminance level of the region of interest may be perceived as one different from the actual luminance level thereof owing to optical illusion.

If such possible false perception of the luminance level by optical illusion is left unsolved, a misdiagnosis would result. Accordingly, for example, in order to reduce the influence of the optical illusion on a B mode image, the image processing such as to allow temporally varying a color or color tone of regions, in the B mode image, in which the luminance level is the same or within a definite range, and causing the monitor 5 to display, is applied to the B mode image by the image processing device 20. However, when the Doppler image information is expressed by luminances, the similar image processing may be applied to the Doppler image.

With such being the situation, first, in the step S2, a user designates a display method for display color of a B mode image by using the input device 4. The items to be designated as the display method for the display color of the B mode image is an altered color in regions in which the luminance level is the same, the display time when displaying, by the altered color, the regions in which the luminance level is the same, and the order of displaying the regions to be displayed in the altered color.

The altered color can be selected from arbitrary colors such as achromatic color, red, blue, and the like, by the user operating the input device 4. The time period for which a specified region is displayed by the altered color, such as one sec, two sec, or the like, can be selected by the user operating the input device 4. The order of displaying regions to be displayed in the altered color can be selected, by the user operating the input device 4, from some display orders, such as: 1) a display order in which the display is performed from a region having a higher luminance level toward a region having a lower luminance level (i.e., descending order), and 2) a display order in which the display is performed from a region having a lower luminance level toward a region having a higher luminance level (i.e., ascending order).

Moreover, it is also possible to designate whether the regions to be displayed in the altered color is all regions, or regions in which the luminance level is within a predetermined range.

In order to set such parameters, including the altered color, display time, display region, display order of displaying display regions, for designating alteration conditions of the display color of a B mode image, setting screen information is generated and written into the image memory 12 by the coloring condition setting portion 24. Then, the setting screen information on the parameters is given to the monitor 5 by the image synthesizing circuit 10 and displayed thereon. Thereby, the user can set each of the parameters by operating the input device 4 while making reference to the setting screen.

The setting information on parameters such as altered colors, and the like inputted into the input device 4 is provided to the coloring condition setting portion 24, and the coloring condition setting portion 24 gives it to the luminance scale altering portion 22 and the image reconstructing portion 23.

Next, using the input device 4 such as switches 4b, the user gives a start command for image processing such as to allow temporally varying the display color of a B mode image to thereby cause the monitor 5 to display it, to the image processing device 20 formed inside the apparatus main body 2 of the ultrasonic diagnostic apparatus 1.

Then, in the step S3, image processing of the image data stored in the image memory 12 is started in accordance with the parameter information given by the coloring condition setting portion 24 by the luminance scale altering portion 22 and the image reconstructing portion 23 in the image processing device 20 so that some display color of the image data is continuously displayed with an altered color for a definite time period.

Figure 4:
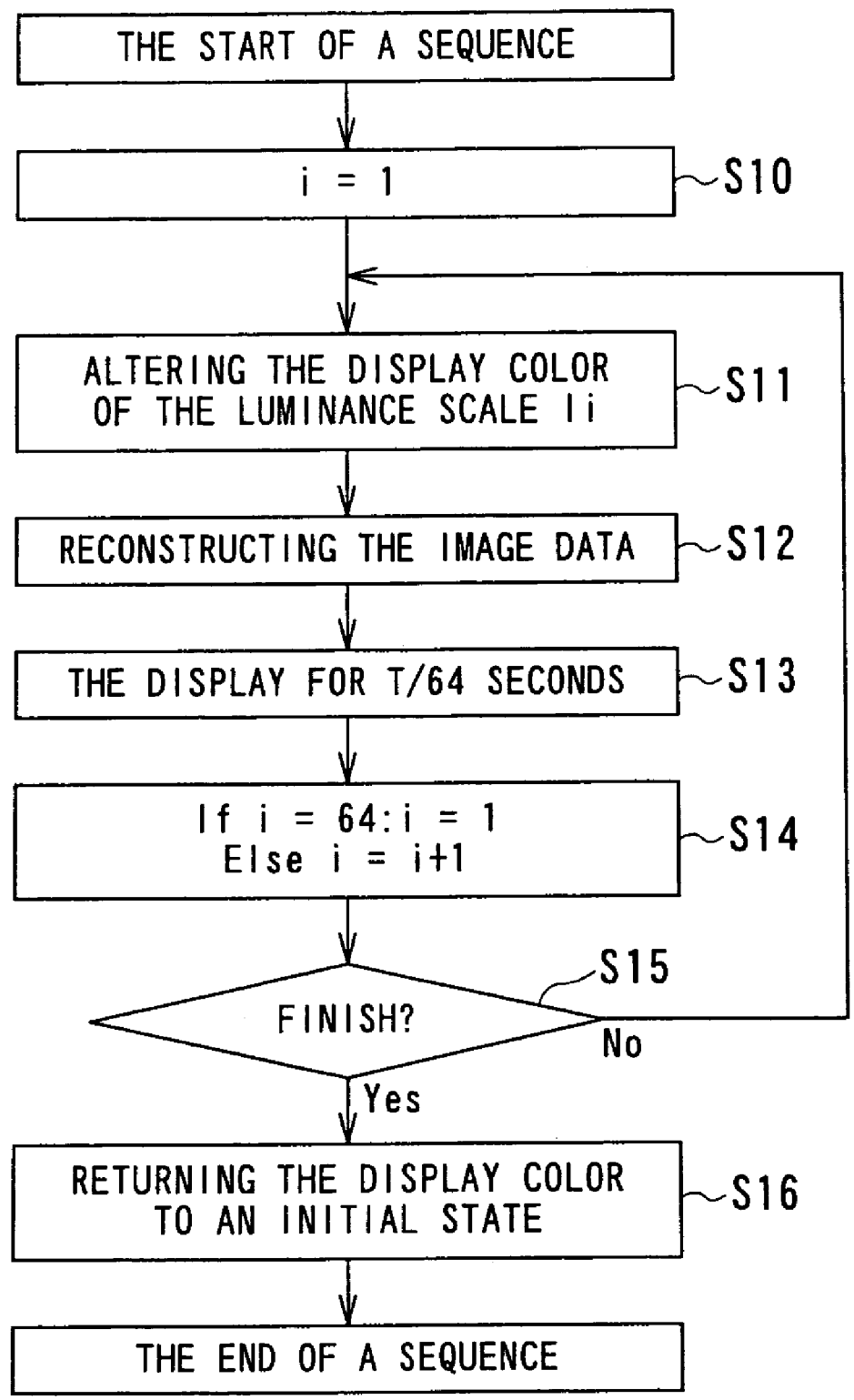
FIG. 4 is a flowchart showing a procedure of image processing for altering a display color of the image data by the image processing apparatus shown in FIG. 2.

FIG. 4 is a flowchart showing a procedure of image processing for altering a display color of the image data by the image processing apparatus 20 shown in FIG. 2. The symbols including S with a number in FIG. 4 indicate each step of the flowchart.

Here, description will be made of the case where the luminance of gray scale is expressed by 64 gradation, and the user designates the altered color as "blue", designates the display time for the altered color as T sec, and designates the display order of the display region to be displayed in the altered color as the "ascending order of luminance level". The luminance gradation values are assumed to be I1, I2, . . . , I64 in ascending order.

First, in the step S10, the luminance scale altering portion 22 determines a luminance gradation value Ii to alter the display color into an altered color, in the luminance scale. Since the display order of the display regions to be displayed in the altered color has been designated as the ascending order of luminance level, 1 is substituted for i, and thus the luminance scale having the lowest luminance gradation value I1 is determined as an alteration target of the display color.

Next, in the step S11, the luminance scale altering portion 22 takes the display color of the luminance scale with the luminance gradation value I1 determined as the alteration target of the display color, as blue color, which is an altered color, and generates a new luminance scale. The generated luminance scale is provided to the image reconstructing portion 23.

Then, in the step S12, the image reconstructing portion 23 reads the image data to be displayed, from the image memory 12, and based on the new luminance scale generated by the luminance scale altering portion 22, reconstructs the image data so that the display color in the region in which the luminance gradation value is I1 is expressed in blue color, which is the altered color. Furthermore, the image reconstructing portion 23 writes the parameter information given by the coloring condition setting portion 24, i.e., the display time information to the effect that the display is to be performed for T/64 sec, and the display order information generated so that the display order becomes the "ascending order of luminance level", into the image memory 12 so as to be appended to the image data.

On the other hand, the luminance scale display portion 21 generates luminance scale information for causing the extra monitor 5 to display the luminance scale generated by the luminance scale altering portion 22, as an image, and writes it into the image memory 12. For example, this luminance scale information is generated as bar-form image information in which the portion of the luminance gradation value I1 is displayed in blue color.

Then, in the step S13, the image data including the color information on blue color and the luminance scale information each written in the image memory 12 are read and synthesized by the image synthesizing circuit 10, and then they are given to the monitor 5 in accordance with the display time information and display order information. As a result, the subject' gray scale tomographic image in which only the region of I1, ranking first in display order and having the lowest luminance gradation value, is displayed in blue color, is displayed on the monitor 5 for T/64 sec. Furthermore, in the vicinity of the tomographic image of the subject P, displayed is a bar-form image showing a luminance scale in which the portion of the luminance gradation value I1 has become blue color.

Also, as required, after the original image data using no altered color has been read from the image memory 12 by the image synthesizing circuit 10, it is provided to the monitor 5, and displayed in parallel with image data generated by the image reconstructing portion 23 in a side-by-side manner.

Next, in the step S14, the luminance scale altering portion 22 determines the luminance level of I2, which is a second lowest luminance gradation value, as a luminance level to be displayed in blue color as the altered color. That is, with the luminance gradation value being Ii, 2 is substituted for i.

Thereafter, in the step S15, the image reconstructing portion 23 determines whether a command to the effect that the display of the image data using the altered color should be finished, has been inputted form the input device 4. If the display of the image data using the altered color is to be continued, again according to the same procedures as those of the step S11 and subsequent steps, the display color in the region of I2, which is a second lowest luminance gradation value, is taken as blue color, while the display color at the luminance level of the luminance gradation value I1 is returned to the initial gray scale display color. Then, image data reconstructed in accordance with the newly generated luminance scale is displayed on the monitor 5 for T/64 sec. Thereafter, a luminance level of I3, which is a third lowest luminance gradation value, is determined as an alteration target of display color.

These alterations of the display color at luminance levels different in the luminance gradation value Ii and displays for T/64 sec are sequentially repeated in the order designated by the display order information until the image reconstructing portion 23 determines, in the step S15, that the command to the effect that the display of the image data using the altered color should be finished, has been inputted form the input device 4. Thus, when a circuit of the alteration of display color has been made up to the luminance level of a luminance gradation value I64, the display time of the image data becomes T sec.

Figure 5:
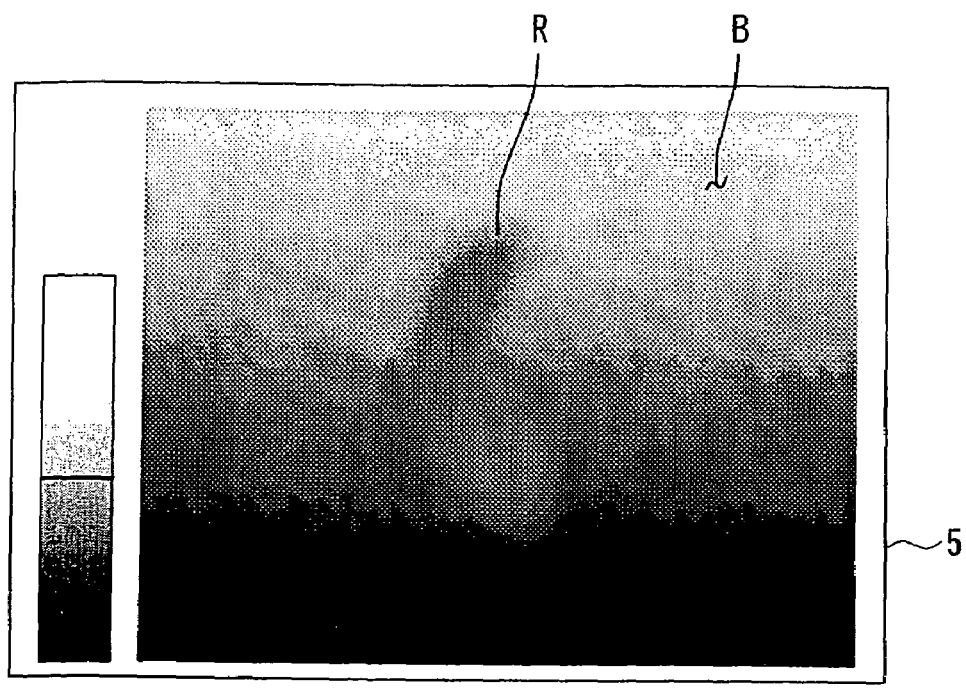
FIG. 5 is a diagram showing an example of image data before performing image processing for altering a display color to an alteration color, displayed on the monitor by the image processing apparatus shown in FIG. 2.
Figure 6:
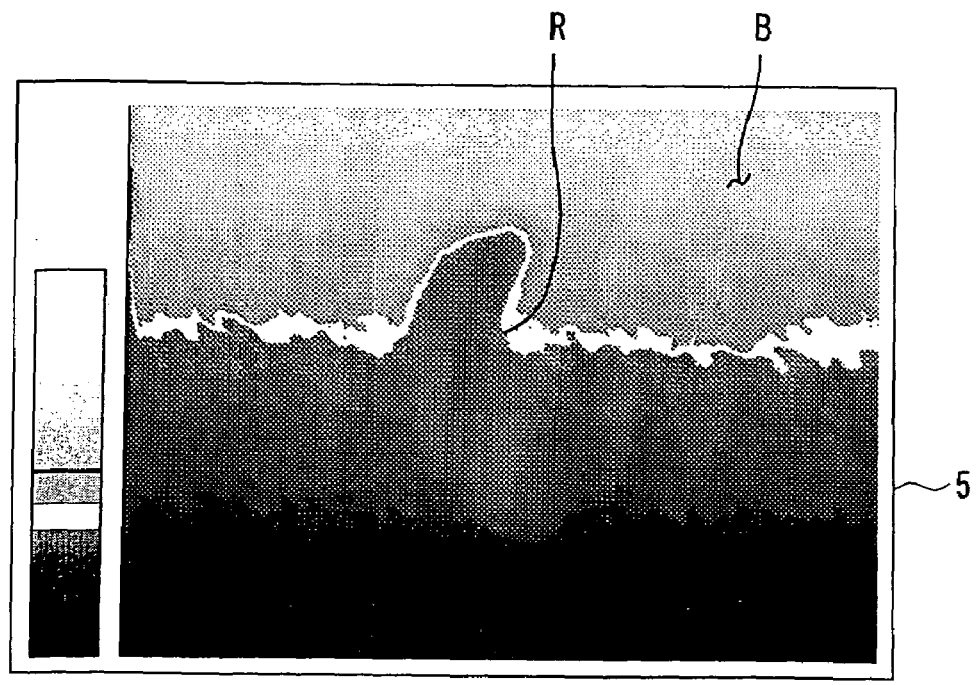
FIG. 6 is a diagram showing an example of image data at a certain time after performing image processing for altering a display color to an alteration color, displayed on the monitor by the image processing apparatus shown in FIG. 2.

FIG. 5 is a diagram showing an example of image data before performing image processing for altering a display color to an alteration color, displayed on the monitor 5 by the image processing apparatus 20 shown in FIG. 2. FIG. 6 is a diagram showing an example of image data at a certain time after performing image processing for altering a display color to an alteration color, displayed on the monitor 5 by the image processing apparatus 20 shown in FIG. 2.

The images in FIGS. 5 and 6 can also be displayed side by side by dividing the display region of the monitor 5. As illustrated in FIG. 5, in the tomographic image of the subject P, for example, the luminance of the background B is different part by part, whereas that of the region R of interest is constant. In the case of such a tomographic image, the luminance of the region R of interest is felt as being different from the actual luminance thereof owing to optical illusion. Thus, the perception for luminance of the region R of interest depends on the luminance of the background B.

On the other hand, as shown in FIG. 6, by displaying the display color at a specified luminance level of the background B in another color, and after a lapse of a definite time, returning the display color at the pertinent luminance level to the initial color while displaying the display color at another luminance level in another color, it is possible reduce the influence of optical illusion. That is, because color tones in the background section at the same luminance level temporally change, it can be easily determined whether, for example, the entire region R of interest has the same luminance, or there are differences in the luminance level depending on a location.

Moreover, in the step S15 in FIG. 4, once the image reconstructing portion 23 determines that the command to the effect that the display of the image data using the altered color should be finished, has been inputted from the input device 4, in the step S16, the image reconstruction processing of the image data stops, and the original image data before being subjected to the image processing is provided to the monitor 5, whereby the display color of the image data is returned to an initial state and displayed on the monitor 5.

According to the above-described ultrasonic diagnostic apparatus 1, it is possible to improve the visibility of contrast without subjecting the luminance contrast in the region R of interest or the degree of luminance variation, to disturbance by surrounding luminances or the temporal variations of luminance. Also, with virtue of this improvement effect in the contrast visibility, the drawing property of diagnostic image is not impaired, which allows the achievement of better diagnostic information.

Meanwhile, for the purpose of improving the visibility of contrast, for example, generating a luminance scale by multiple colors like a rainbow, and displaying a diagnostic image in the style of a contour-line display would allow portions at the same luminance level to be grasped. However, in many cases, such a method would seriously impair the drawing property in the conventional diagnostic image, which would eventually end up providing no useful diagnostic information.

Additionally, the difference between luminances can be compared also by a quantitative measuring method such as measurement of luminance histogram of the region R of interest. However, such a method not only requires time and efforts for making a shift to a measurement mode, but also makes it difficult to grasp the entire region of the diagnostic image since the measurement must be generally performed locally.

On the other hand, according to the present ultrasonic diagnostic apparatus 1, only by operating the input device 4 such as the switches 4b, an outline on the diagnostic image displayed on the monitor 5 looks like it is sweeping the diagnostic image, and hence the drawing property of the entirety of the conventional B mode image is hardly impaired, and the difference in the luminance can be more clearly known.

In addition, all of three kinds of parameters, such as an alteration color, needed at image processing can be changed by a user in the ultrasonic diagnostic apparatus 1 or the ultrasonic diagnostic apparatus 1. However, some of kinds of parameters may be fixed so that a user don't change them.

Furthermore, the image processing apparatus 20 of the ultrasonic diagnostic apparatus 1 may perform image processing to moving image displayed on real time as well as still image.

The luminance level Ii, which constitutes an alteration target of the display color in image processing, is not limited to a single luminance level Ii. For example, the alterations of display colors may concurrently be performed with respect to luminance levels within a definite range relative to a specified Ii, i.e., luminance levels from Ii−m to Ii+m (here, m is an arbitrary integer; when (i−m)<0, the value (i−m) is assumed to be 0, and when (i−m)>64, the value (i−m) is assumed to be 64).

On the other hand, without providing the image reconstructing portion 23 with the function of generating display time information for designating the alteration time for the display color, the image processing by the image processing device 20 can also be limited to merely processing for altering the display color in a particular region within a luminance level in a static image or moving image into a designated altered color. In this case, the information designating the altered color and the range information on the luminance level at which the display color is to be altered into the altered color, are inputted into the input device 4. Then, the information designating the altered color and the range information on the luminance level at which the display color is to be altered into the altered color are given from the coloring condition setting portion 24 to the luminance scale altering portion 22, and a new luminance scale is generated by the luminance scale altering portion 22.

The image reconstruction processing with respect to the image data stored in the image memory 12 is performed by the image reconstructing portion 23 using the luminance scale newly generated by luminance scale altering portion 22, and the image reconstructed based on the new luminance scale is provided to the monitor 5 through the image synthesizing circuit 10 and displayed thereon.

The image processing device 20 may have an interface function so that the user can input the range information on the luminance level at which the display color is to be altered into an altered color, from the input device 4 via the luminance scale image displayed on the monitor 5 in the form of a bar.

Figure 7:
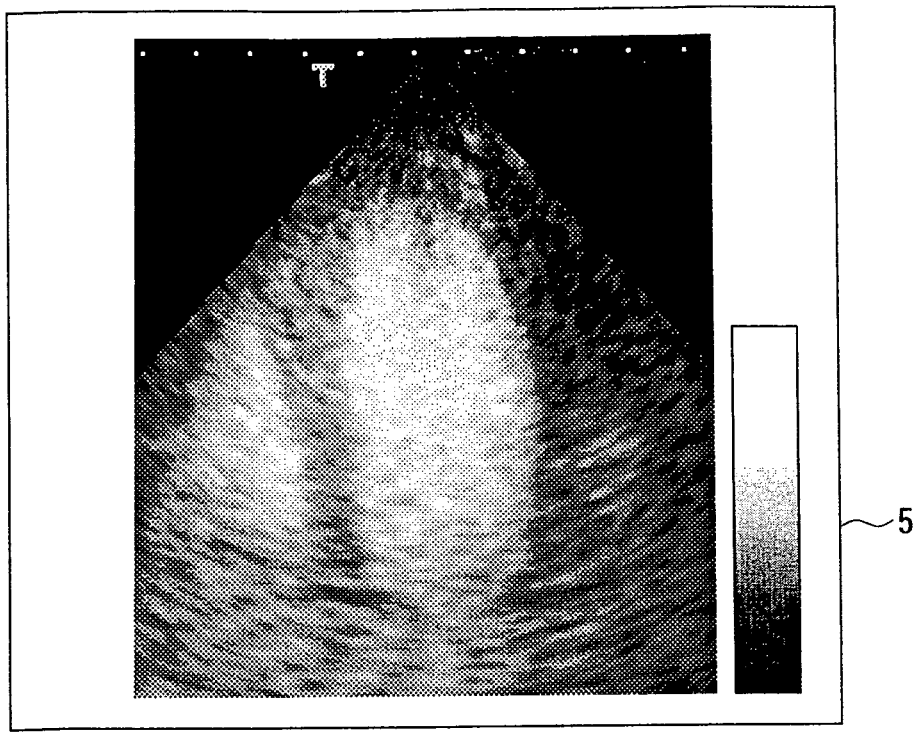
FIG. 7 is a diagram showing an image displayed by luminance according to a gray scale and a luminance scale image of bar form.

FIG. 7 is a diagram showing an image displayed by luminance according to a gray scale and a luminance scale image of bar form.

With respect to a gray scale image shown in FIG. 7, for example, the information on designating altered color and the range information on luminance level at which the display color is to be altered into the altered color is inputted from the input device 4 so that the region in which the luminance level is beyond a definite value is displayed in black color.

Figure 8:
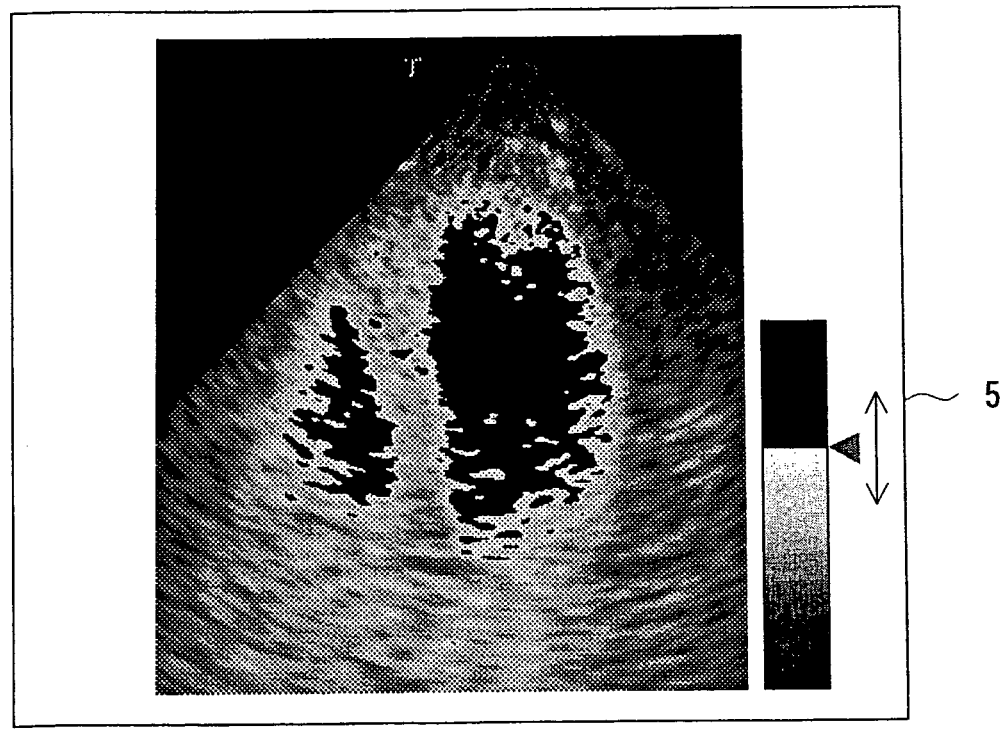
FIG. 8 is a diagram showing an example of the image shown in FIG. 7 whose region of some luminance levels is displayed in an alteration color.

FIG. 8 is a diagram showing an example of the image shown in FIG. 7 whose region of some luminance levels is displayed in an alteration color.

FIG. 8 is an image, of the image in FIG. 7, obtained by performing image reconstruction processing such that the region in which the luminance level is beyond a definite value is displayed in black color. As shown in FIG. 8, the region in which the luminance level is beyond a definite value is displayed in black color, and the luminance level portion in a corresponding bar-form luminance scale image is also displayed in black color.

A marking display is applied to the location of a standard luminance level in the bar-form luminance scale image. The range information on luminance level can also be altered by moving the marking display by the input device 4.

In this manner, not only the display color of the region R of interest, but also the display color of a part of the background that is unimportant for diagnosis, are altered into an altered color and displayed, whereby the influence of optical illusion can be reduced, resulting in enhanced contrast visibility. In particular, in the case where the luminance level of the background is different depending on a location, a display in a single altered color could even further reduce the influence of optical illusion.

The altered color is not limited to a single color. Altered colors different from one luminance level to another can be used to perform a display. In addition, it is also possible to apply processing such as smoothing processing to a portion displayed in an altered color and a portion displayed in an original display color so that the boundaries between these portions are smoothly displayed.

Figure 9:
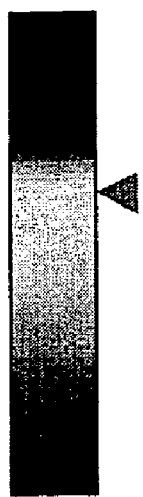
FIG. 9 is a diagram showing an example of alteration colors setup at image processing by the image processing apparatus shown in FIG. 2.
Figure 10:
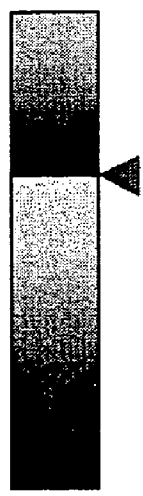
FIG. 10 is a diagram showing another example of alteration colors setup at image processing by the image processing apparatus shown in FIG. 2.

FIG. 9 is a diagram showing an example of alteration colors setup at image processing by the image processing apparatus 20 shown in FIG. 2. FIG. 10 is a diagram showing another example of alteration colors setup at image processing by the image processing apparatus 20 shown in FIG. 2.

FIG. 9 shows a bar-form luminance scale image in which boundaries between a region having a luminance level beyond a definite value and displayed in an altered color, and a region having a luminance level below the definite value and displayed in an original color, are smoothly displayed. On the other hand, FIG. 10 shows a bar-form luminance scale image arranged so that a region having a luminance level beyond a definite value can be displayed in altered colors different from one luminance level to another.

In this way, various altered colors can be arbitrarily set in correspondence with the occurrence conditions of optical illusion.

Figure 11:
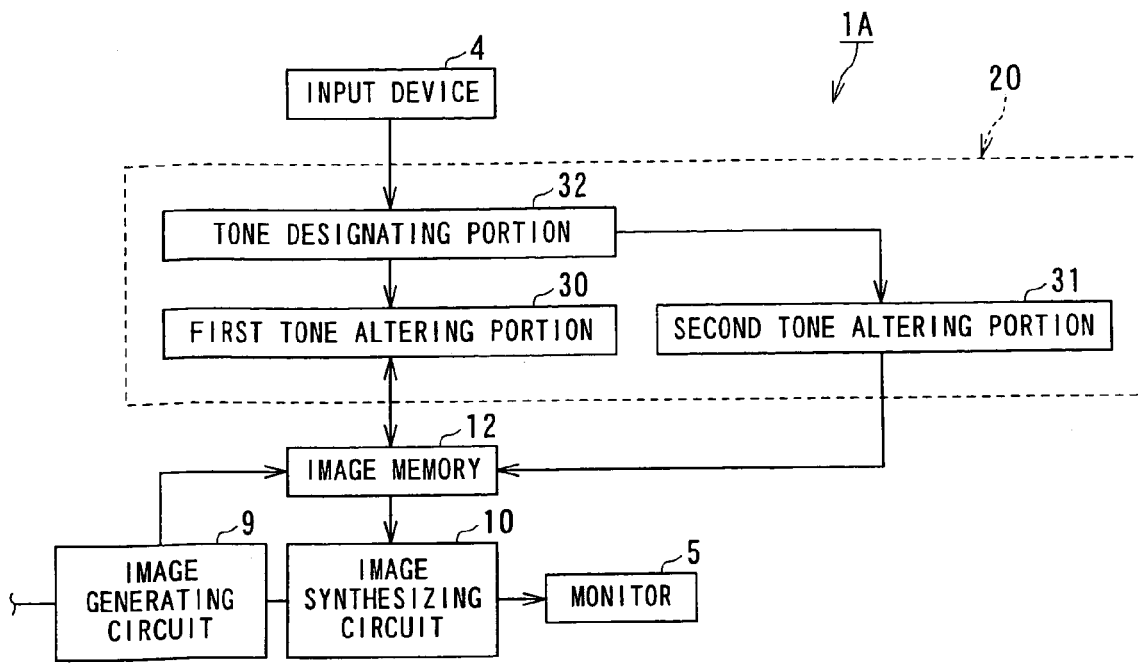
FIG. 11 is a block diagram showing an ultrasonic diagnostic apparatus according to a second embodiment of the present invention.

FIG. 11 is a block diagram showing an ultrasonic diagnostic apparatus according to a second embodiment of the present invention.

In the ultrasonic diagnostic apparatus 1A shown in FIG. 11, detail function of each component of the apparatus main body 2 and functional construction of the image processing apparatus 20 are different from those of the ultrasonic diagnostic apparatus 1 shown in FIG. 1. Other constructions and operations of the ultrasonic diagnostic apparatus 1A are not different from those of the ultrasonic diagnostic apparatus 1 shown in FIG. 1 substantially. Therefore, only a functional block diagram of the image processing apparatus 20 is to be shown, attaching same number to a same component as that of the ultrasonic diagnostic apparatus 1 and omitting explanation thereof.

The image generating circuit 9 of an ultrasonic diagnostic apparatus 1A shown in FIG. 11 has the function of applying a maximum luminance level holding operation to B mode image information and the Doppler image information received from the B-mode processing unit 7 and the Doppler processing unit 8. This maximum luminance level holding operation is an image processing for reconstructing an image such that the maximum value of luminance level in the past image data is displayed when image data is temporally continuously collected. The maximum luminance level holding operation is effective when blood flows flowing in blood capillaries are extracted from a plurality of pieces of image data collected by temporally continuous scans to thereby acquire blood flow images.

Here, descriptions will be made of the case where the maximum luminance level holding operation is applied to n pieces of image data from a frame F1 to a frame Fn in a time series included in the same time period TL, the image data having been collected in a particular scan. In the maximum luminance level holding operation with respect to the image data from the frame F1 to the frame Fn, the maximum luminance level Pmax (x, y) which is the maximum value is selected from luminance levels of portions spatially mutually corresponding in the frames F1 to Fn, i.e., from luminance levels of portions of which the coordinates (x, y) in the frames F1 to Fn mutually coincide. Thus, new image data is generated.

Here, the image data of a particular frame Fi (here, "i" is an integer satisfying 1≦i≦n) comprises a set of luminance levels Pi (x, y) that are spatially arranged, or merely a set of array data Pi(x) of one-dimensional luminance levels.

The values of Pi(x, y) or Pi(x) can be each calculated as a "signal intensity", "signal amplitude" or "raw data such as RF data" instead of "luminance", but a "luminance level" is adopted herein. Regarding each of these data values, generally, the higher the numeric value, the higher is the echo signal level.

The maximum luminance level holding operation is a calculation in which pixels having the maximum luminance level is selected from pixels spatially corresponding in the frames from F1 to Fn to thereby generate new image data. This calculation can be expressed by the following expression (1).

$$P\max(x,y) = \max[P1(x,y), \ldots, Pn(x,y)] \quad (1)$$

When the maximum luminance level holding operation shown by the processing of the expression (1) is performed every time a new frame included in the same sound pressure period TL is collected in a dynamic imaging of blood capillaries using a contrast medium, and the acquired image data is displayed, appearances such that the blood capillaries are sequentially enhanced by the contrast medium with the passage of time as viewed from the user side can be projected onto the screen.

The algorism for implementing such a maximum luminance level holding operation is not limited to the processing shown in the expression (1). An effect similar to that of this processing can also be produced by, for example, the processing shown in the expression (2). Here, let the pixel luminance at coordinates (x, y) of the current tomographic image frame Fi to be Pi (x, y), and let the pixel luminance of a tomographic image frame Fi−1 that immediately precedes Fi in time, to be Pi−1 (x, y). Regarding two different frames, image calculation processing by the following expression (2) is sequentially performed with respect to i=2 to n, and thereby maximum luminance level holding operation can be performed.

| If | Pi (x, y) > Pi − 1 (x, y) | (2) |
|---|---|---|
| Then | Pi (x, y) = Pi (x, y) | |
| Else | Pi (x, y) = Pi − 1 (x, y) | |

The algorism shown in the expression (2) compares respective luminance levels of pieces of image data regarding pre-stage and post-stage frames, and values of only pixels having higher luminance level are updated. Also by the display of the image data obtained in this way, the user can observe appearances as if blood capillaries are sequentially enhanced with the passage of time, as moving images.

Next, another example of preferable methods for generating a blood flow image including a blood capillary will be described. This method generates new image data by applying calculation including weighting to n pieces of image data from the frames F1 to Fn included in the same time period TL. Here, the calculation including weighting refers to calculation expressed by the following expression (3).

| If | Pi (x, y) > Pi − 1 (x, y) | (3) |
|---|---|---|
| Then | Pi (x, y) = A * Pi (x, y) + (1 − A) * Pi − 1 (x, y) | |
| Else | Pi (x, y) = (A − 1) * pi (x, y) + A * Pi − 1 (x, y) | |

In the expression (3), letting A to be a value below 1 and close to 1 (e.g., 0.99), maximum luminance level holding operation is performed in a shorter time, and an operation that attenuates the luminance held by the maximum luminance level holding operation in a longer time can be expected. Also by image data obtained by such a method, the user can observe images as if blood capillaries are sequentially enhanced with the passage of time.

The image data generated by the maximum luminance level holding operation with the image generating circuit 9 in this way is stored into the image memory 12 together with the original image data used in the maximum luminance level holding operation, as required.

On the other hand, the image processing apparatus 20 built in the ultrasonic diagnostic apparatus 1A functions as a first tone altering portion 30, a second tone altering portion 31 and a tone designating portion 32 by the control processor 11 reading an image processing program.

The first tone altering portion 30 has the function of applying the image reconstruction processing for altering the color tones of the image data having been subjected to the maximum luminance level holding operation and stored in the image memory 12, into a predesignated first color tone. The second tone altering portion 31 has the function of applying image reconstruction processing for altering the color tones of the image data having been subjected no maximum luminance level holding operation and stored in the image memory 12, into a predesignated second color tone. Also, the tone designating portion 32 has the function of designating color tones used as the first color tone and the second color tone based on information designating a color tone, received from the input device 4.

Meanwhile, all or a part of each of the maximum luminance level holding operation function and the processing function of the image synthesizing circuit 10 each included in the image generating circuit 9 may be disposed on the image processing device 20 side.

Next, the operation of the ultrasonic diagnostic apparatus 1A will be described.

Figure 12:
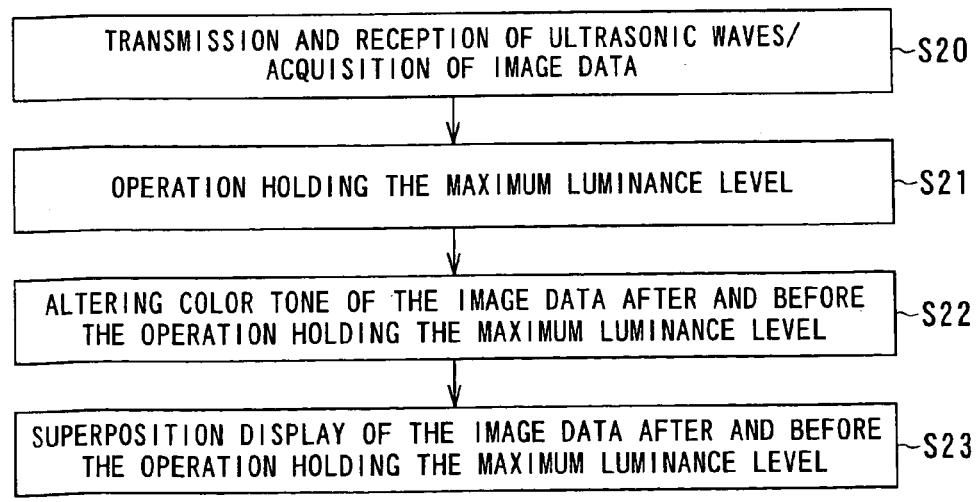
FIG. 12 is a flowchart showing an flow for indicating a diagnostic image by the ultrasonic diagnostic apparatus shown in FIG. 11.

FIG. 12 is a flowchart showing an flow for indicating a diagnostic image by the ultrasonic diagnostic apparatus 1A shown in FIG. 11. The symbols including S with a number in FIG. 12 indicate each step of the flowchart.

Now, in the step S20, once ultrasonic waves have been transmitted to and received from the subject P over a plurality of times, echo signals in a time series are sequentially acquired. Thus, tomographic images (B mode images) that are luminance-displayable for a plurality of frames, of the subject P are generated from the echo signals.

Next, in the step S21, maximum luminance level holding operation is sequentially applied to spatially corresponding pixels of the tomographic image of the subject P by the image generating circuit 9, and thereby image data is generated. The image data generated by the maximum luminance level holding operation is written into the image memory 12 together with image data having been subjected to no maximum luminance level holding operation and temporarily stored into the image memory 12.

Then, in the step S22, the first tone altering portion 30 reads the image data having been subjected to the maximum luminance level holding operation and stored in the image memory 12, and alters the color tone of the image data into the first color tone predesignated. On the other hand, the second tone altering portion 31 reads image data having been subjected no maximum luminance level holding operation and stored in the image memory 12, and alters the color tone of the image data into the second color tone predesignated.

The image data after the maximum luminance level holding operation is data for an image, to be display by luminance with gray scale, comprising pixels Pi (x, y) generated by the maximum luminance level holding operation with respect to a plurality of frames of image data obtained by performing scans in the subject P. The B mode image data having been subjected no maximum luminance level holding operation is also image data that is displayed by luminance with gray scale. The first tone altering portion 30 and the second tone altering portion 31 apply image reconstruction processing to the above-described image data so that these image data become image data that can be expressed by the first and second color tones, respectively.

As a consequence, the image data after the maximum luminance level holding operation does not become image data to be displayed by luminance with gray scale, but becomes image data of which the first color tone alone changes with the luminance of the original B mode image reflected. Similarly, the image data having been subjected to no maximum luminance level holding operation becomes an image data of which the second color tone alone changes with the luminance of the original B mode image reflected. Each of the image data after having been subjected to the color tone alteration is written into the image memory 12 and stored therein.

Here, the first and second color tones can be arbitrarily set by the user previously inputting information designating a color tone from the input device 4 and by the tone designating portion 32 giving the information designating a color tone received from the input device 4 to the first tone altering portion 30. The tone designating portion 32 generates color tone designation screen information for designating the color tone by the user, and writes it into the image memory 12. Consequently, because the color tone designation screen information is given by the image synthesizing circuit 10 to the monitor 5 and displayed thereon, the user can easily designate the first and second color tones from the input device 4 making reference to the color tone designation screen. Here, the first and second color tones are color tones at least different from each other.

Next, in the step S23, the image synthesizing circuit 10 reads respective image data before and after the maximum luminance level holding operation after the color tone stored in the image memory 12 has been altered, and gives them to the monitor 5 to thereby cause the monitor 5 to superposition-display them so as to be a single image. As a consequence, the color tone of the image having been subjected to the superposition display is determined by the color tones of the respective image data before and after the maximum luminance level holding operation, and the colors of these image data are mixed into another color.

In view of the fact that the color of the image data displayed in the monitor 5 is ultimately expressed in a color tone other than the first and second color tones by the superposition display processing of the image data with the first and second color tones, an arbitrary color tone selection by the user might bring about an unexpected color tone. Accordingly, it is preferable to use a method in which some recommendable combinations of the first and second color tones are set as alternatives in advance, and in which the user selects from among these alternatives.

The simplest methods as implementation means for color tone designation includes a method in which the component(s) of the first color tone is set to any one or two of the basic colors (three primary colors) [red, blue, and green], which are components of gray scale, while the component(s) of the second color tone is set to one or two of the remaining color tone(s). Setting the component(s) of each of the first and second color tones to any of the primary colors [red, blue, and green] not only facilitates the anticipation of a mixed color but also facilitates calculation using the existing color techniques, and allows the image data to be reconstructed for display in a shorter time.

Accordingly, for example, based on the assumption that the first tone is [blue+green] (=Yellow) and the second tone is [red], the tone change of image having been superposition-displayed will be now described.

Figure 13:
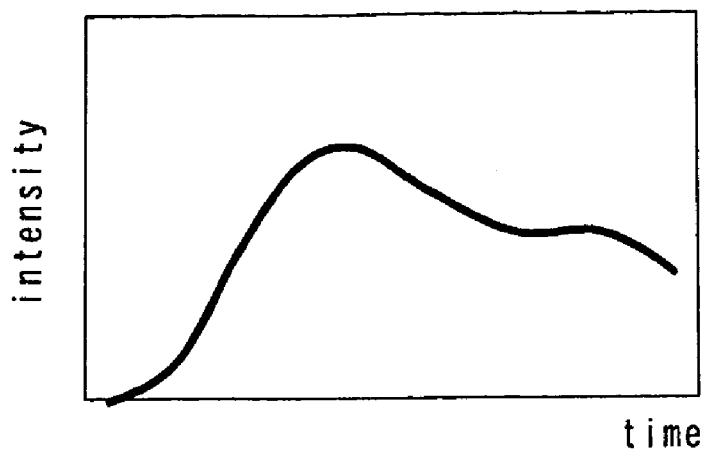
FIG. 13 is a diagram indicating time variation of the luminance level in the case of displaying image data according to signal intensity by the conventional gray scale without performing the maximum luminance level holding operation.
Figure 14:
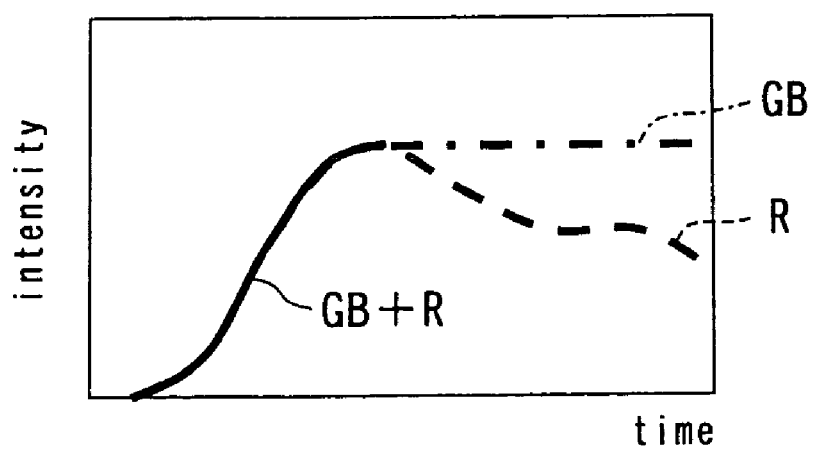
FIG. 14 is a diagram indicating time variation of intensity of each color tone in the case of displaying super positioned image data before and after the maximum luminance level holding operation by using the first and second color tone on the ultrasonic diagnostic apparatus shown in FIG. 11.

FIG. 13 is a diagram indicating time variation of the luminance level in the case of displaying image data according to signal intensity by the conventional gray scale without performing the maximum luminance level holding operation. FIG. 14 is a diagram indicating time variation of intensity of each color tone in the case of displaying super positioned image data before and after the maximum luminance level holding operation by using the first and second color tone on the ultrasonic diagnostic apparatus 1A shown in FIG. 11.

In FIG. 13 and FIG. 14, the horizontal axis indicates time and the vertical axis indicates intensity of each color tone determined according to each value of signal intensity.

As shown in FIG. 13, for example, when the contrast medium flows into the subject P, and after the signal intensity of echo signals has monotonously increased, the contrast medium flows out of the region R of interest, and the signal intensity of the echo signal decreases, the luminance level of the image data increases and decreases according to gray scale in response to the signal intensity. However, if the luminance level of the region R of interest such as a tumor is constant and the luminance level of surrounding tissues minutely increases, then, the conventional B mode image shown in FIG. 13 might provide the illusion that the luminance of the tumor section be decreasing.

On the other hand, as shown in FIG. 14, in the case where the image data before and after the maximum luminance level holding operation is superposition-displayed using the first and second tones, the intensities of the first and second tones concurrently increase while the contrast medium flows into the subject P, and the luminance level of the B mode image before the maximum luminance level holding operation monotonously increases. Consequently, if the setting is performed so that, relative to the signal intensity value of 100, the intensities of these tons become as follows: (R, G, B)=(100, 100, 100) [here, R, G, and B refer to red, green, and blue, respectively], then, all tones of red, blue, and green become equal in the intensity, so that the diagnostic image of the mixed color having been superposition-displayed assumes gray color.

In FIG. 14, the solid line shows the intensity (R, G, B) of the color tone in case the intensity of each color tone corresponds, the chain line shows the intensity (G, B) of the first color tone (yellow) and a dotted line shows the intensity (R) of the second color tone (red).

Next, once the inflow of the contrast medium has become constant, for example, once the signal intensity of echo signals has reached 200, the increase in luminance level of the original B mode image stops. Furthermore, once the contrast medium has flowed out of the region R of interest and the decrease in the luminance level of the original B mode image has occurred, the intensity of the first tone (yellow) of the image data after the maximum luminance level holding operation, i.e., (G, B)=(200, 200) is held, while the intensity of only the second tone (red) of the image data before the maximum luminance level holding operation decreases. As a consequence, for example, once the intensities of the first and second tones of the diagnostic image subjected to a superposition display have become (R, G, B)=(160, 200, 200), the diagnostic image is displayed in a color with a yellowish tone.

In this manner, according to the diagnostic image which has been superposition-displayed in the tone by the ultrasonic diagnostic apparatus 1A as shown in FIG. 14, when the luminance level of a specified region of the diagnostic image decreases, or when it again increases after it has decreased once, since the tone of the relevant region changes, it is possible to avoid the influence of optical illusion and easily identify the change in the luminance level, irrespective of variations in the around luminance levels. At this time, the drawing property in the conventional diagnostic images is prevented from being impaired.

Figure 15:
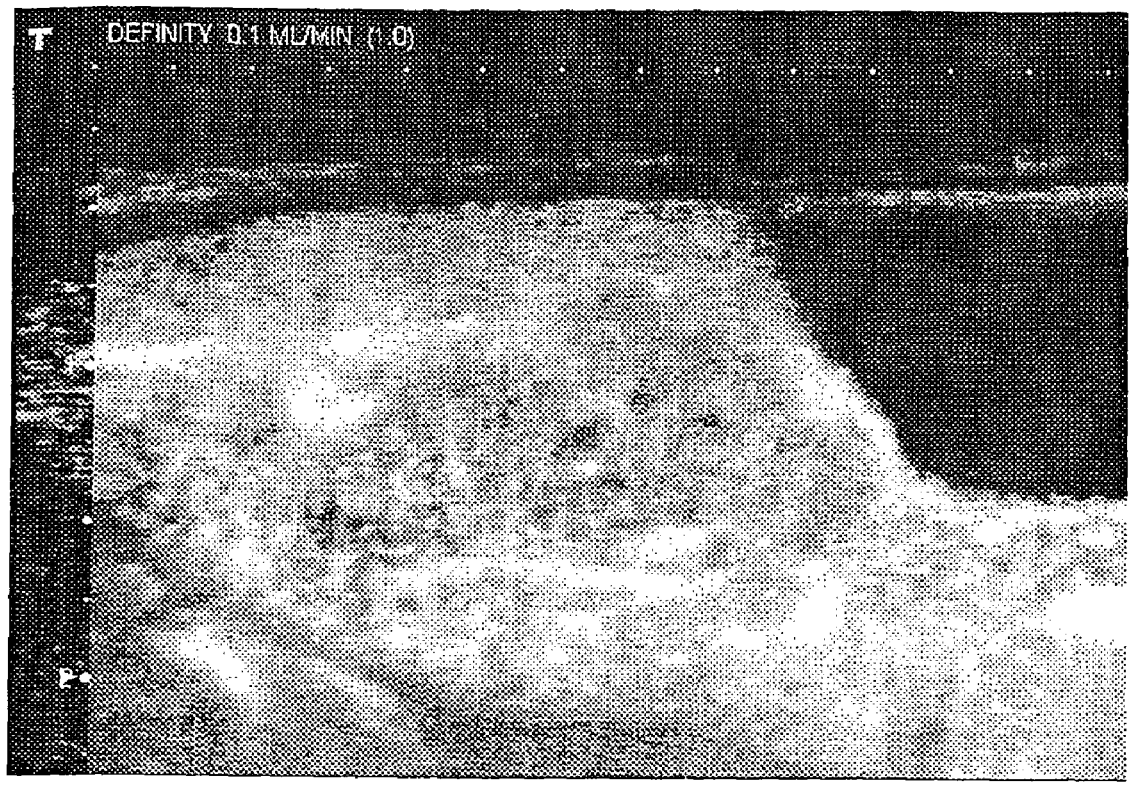
FIG. 15 is a diagram showing an example of tomogram of the subject generated by the ultrasonic diagnostic apparatus shown in FIG. 11.

FIG. 15 is a diagram showing an example of tomogram of the subject P generated by the ultrasonic diagnostic apparatus 1A shown in FIG. 11.

In FIG. 15, when the luminance level of a particular region decreases after it has reached the maximum value, the tone is displayed in a changed state, which allows the avoidance of false perception, in the luminance level, due to optical illusion.

According to the ultrasonic diagnostic apparatus 1A as described above, it is possible to reduce the influence of optical illusion and improve contrast visibility as in the case of the ultrasonic diagnostic apparatus 1 shown in FIG. 1. That is, even if the luminance of the background in a diagnostic image varies with time, the presence/absence of variation in the luminance level of the region R of interest can be easily identified based on variations in the tone.

Figure 16:
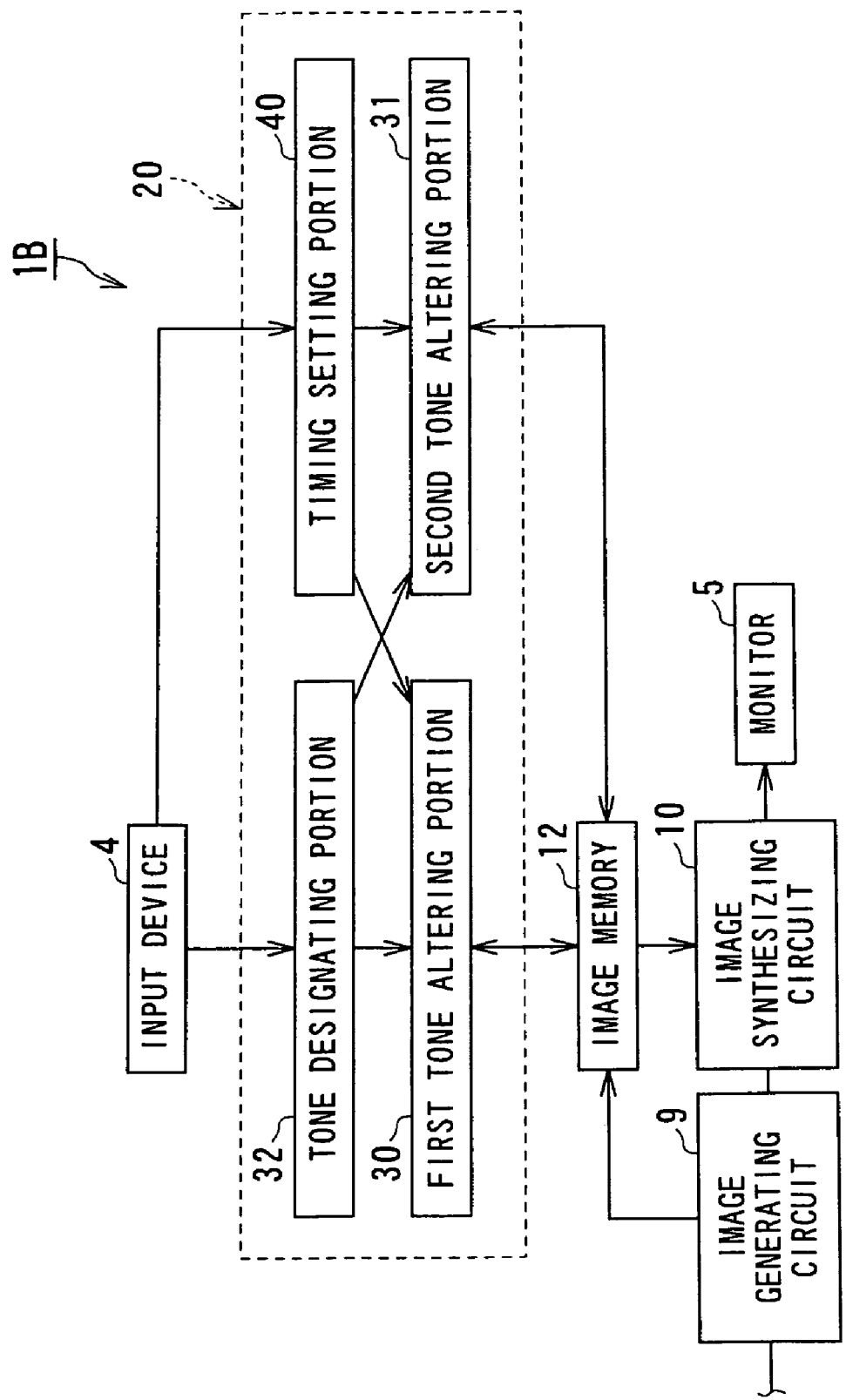
FIG. 16 is a block diagram showing an ultrasonic diagnostic apparatus according to a third embodiment of the present invention.

FIG. 16 is a block diagram showing an ultrasonic diagnostic apparatus according to a third embodiment of the present invention.

In the ultrasonic diagnostic apparatus 1B shown in FIG. 16, detail function of each component of the apparatus main body 2 and functional construction of the image processing apparatus 20 are different from those of the ultrasonic diagnostic apparatus 1A shown in FIG. 11. Other constructions and operations of the ultrasonic diagnostic apparatus 1B are not different from those of the ultrasonic diagnostic apparatus 1A shown in FIG. 11 substantially. Therefore, only a functional block diagram of the image processing apparatus 20 is to be shown, attaching same number to a same component as that of the ultrasonic diagnostic apparatus 1A and omitting explanation thereof.

The image processing apparatus 20 built in the ultrasonic diagnostic apparatus 1B functions as a first tone altering portion 30, a second tone altering portion 31, a tone designating portion 32 and a timing setting portion 40. The first tone altering portion 30 has function to read the image data at the time set by the timing setting portion 40 from the image data of the time series saved in the image memory 12 to perform image reconstruction processing for altering color tone of the image data to the first color tone predetermined and function to write the image data performed the processing to the image memory 12. The second tone altering portion 31 has function to read the image data after the time set by the timing setting portion 40 from the image data of the time series saved in the image memory 12 to perform image reconstruction processing for altering color tone of the image data to the second color tone predetermined and function to write the image data performed the processing to the image memory 12.

The tone designating portion 32 has function to designate color tones used for the first color tone and the second color tone according to designating information of color tone given from input device 4.

The timing setting portion 40 has function to receive timing setting information input into the input device 4 such as switches 4b to give time information of image whose color tone is to be altered to the first tone altering portion 30 and the second tone altering portion 31.

In addition, the image processing apparatus 20 of the ultrasonic diagnostic apparatus 1B may not have function for the maximum luminance level holding operation.

In an ultrasonic diagnostic apparatus 1B, echo signals in a time series are sequentially acquired by the transmission/reception of ultrasonic waves over a plurality of times. Thus, a plurality of frames of image data (B mode images) for displaying by the luminance with gray scale is generated and sequentially stored in the image memory 12. Typically, the image data for displaying by the luminance with gray scale is sequentially provided to the monitor 5 by the image synthesizing circuit 10 and displayed thereon as moving images.

Moreover, once the user has designated an arbitrary timing by the operation of the switches 4b or the like of the input device 4, the timing setting portion 40 receives the information designating the timing inputted in the input device 4, and gives time information on an image to be altered in tone to the first tone altering portion 30 and the second tone altering portion 31. Here, the first tone altering portion 30 reads image data at the time designated by the timing setting portion 40, from the image data in a time series stored in the image memory 12, and after having applied, to the read image data, reconstruction processing for altering the tone into the first tone predesignated, writes the image data performed the image reconstruction processing into the image memory 12.

Furthermore, the second tone altering portion 31 reads image data at the time designated by the timing setting portion 40 and at times subsequent to the above-described time, from the image data in the time series stored in the image memory 12, and after having applied, to the read image data, reconstruction processing for altering the tone into the second tone predesignated, writes the image data after the image reconstruction processing into the image memory 12.

The image synthesizing circuit 10 sequentially reads the image data having the tones generated by the first tone altering portion 30 and the second tone altering portion 31, from the image memory 12, and provides these image data to the monitor 5, and thereby causes the monitor 5 to superposition-display them as moving images. Here, for example, the first tone is assumed to be [blue+green] (=yellow), and the second tone is assumed to be [red].

Figure 17:
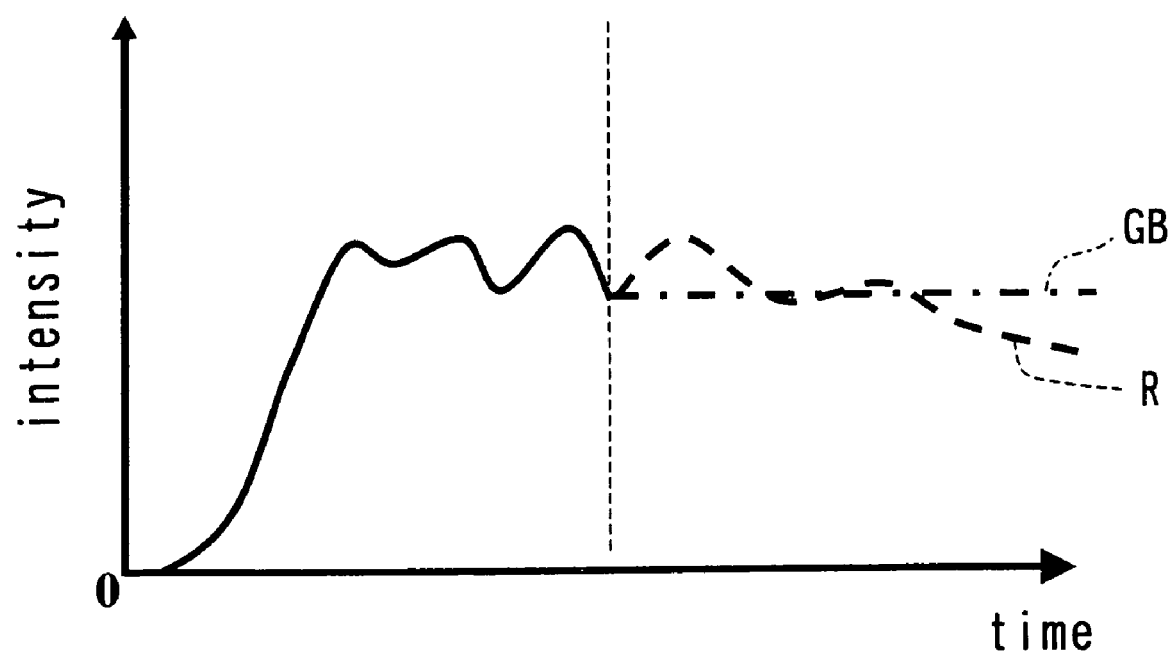
FIG. 17 is a conceptual diagram showing time variation of color tone of the super positioned diagnostic image displayed on the monitor of the ultrasonic diagnostic apparatus shown in FIG. 16.
Figure 18:
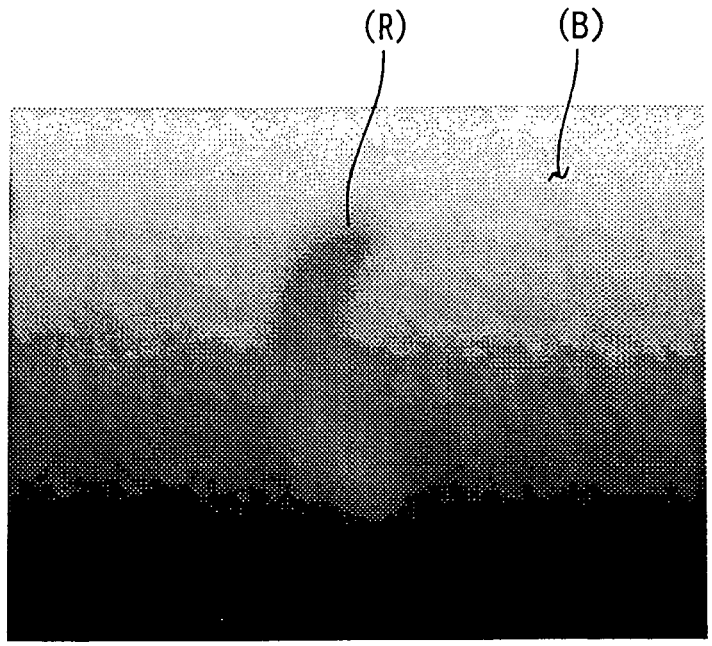
FIG. 18 is a real image which explains an example case optical illusion is to be a problem on diagnosis of a luminance contrast ratio.
Figure 19:
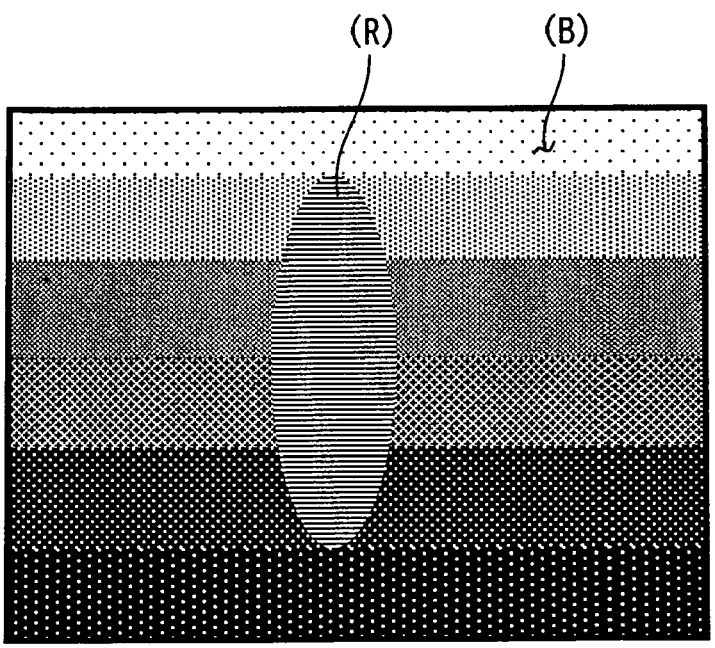
FIG. 19 is an illustration image which explains an example case optical illusion is to be a problem on diagnosis of a luminance contrast ratio.

FIG. 17 is a conceptual diagram showing time variation of color tone of the super positioned diagnostic image displayed on the monitor 5 of the ultrasonic diagnostic apparatus 1B shown in FIG. 16.

In FIG. 17, the horizontal axis indicates time and the vertical axis indicates intensity of each color tone determined according to each value of signal intensity. In FIG. 17, the solid line shows the intensity (R, G, B) of the color tone in case the intensity of each color tone corresponds, the chain line shows the intensity (G, B) of the first color tone (yellow) and a dotted line shows the intensity (R) of the second color tone (red).

As indicated by a solid line in FIG. 17, for example, when the contrast medium flows into the subject P, and the signal intensity of echo signals monotonously increases up to the local maximum value, and thereafter the contrast medium flows out/in with respect to the region R of interest and the signal intensity of echo signals increases and decreases, the luminance level of the image data increases and decreases according to gray scale in response to the signal intensity.

When the user want to grasp the change in the luminance level in the region R of interest after a particular time, for example, the user want to know whether the luminance level in the region R of interest has become constant, the user inputs the information designating the timing on to the input device 4. Then, as indicated by an alternate long and short line in FIG. 17, the tone of image data at the time corresponding to the information designating the timing is altered into the first tone (yellow) by the first tone altering portion 30, and the image data having the first tone are continuously superposition-displayed. On the other hand, as indicated by a dotted line in FIG. 17, the tone of the image data at the time corresponding to the information designating the timing and at the times subsequent to the above-described time is altered into the second tone (red), and the image data having the second tone are superposition-displayed.

As a result, in the image data subjected to a superposition display, the intensity of the image data expressed by the first tone (yellow) becomes constant, whereas the intensity of the image data expressed by the second tone (red) varies in response to the signal intensity of echo signals. Consequently, if the luminance level in the region R of interest is constant, the gray scale tone of the image data subjected to a superposition display is maintained. On the other hand, if the luminance level decreases, the tone changes into yellow, and if the luminance level increases, the tone changes into red. Thereby, the user can identify fluctuations of the luminance level in the region R of interest without being subjected to influences of optical illusion due to variations in the luminance level around the region R of interest.

According to the ultrasonic diagnostic apparatus 1B as described above, it is possible to reduce the influence of optical illusion and enhance contrast visibility as in the case of the ultrasonic diagnostic apparatus 1A shown in FIG. 11. Additionally, with the image at an arbitrary timing designated by the user used as a reference, the variations in the luminance level can be grasped.

In the above-described ultrasonic diagnostic apparatuses 1, 1A, and 1B according to the embodiments of the present invention, the image data may be image-processed as three-dimensional data. In this case, scanning operations with respect to the subject P are performed on a three-dimensional basis, and three-dimensional image data (spatial information) is reconstructed from the acquired echo signals. However, ultimately, when three-dimensional information is displayed on the monitor 5, two-dimensionally projected image data is generated by various projection methods. At this time, with respect to the two-dimensional projection data, a luminance scale is referred to so that two-dimensional projection data are luminance-displayed. As a result, the same image processing as that in the foregoing can be applied to two-dimensional projection data having been luminance-displayed by the image processing device 20.

Furthermore, the ultrasonic diagnostic apparatuses 1, 1A, and 1B in each embodiment may be combined to constitute. Conversely, partial component of ultrasonic diagnostic apparatus 1, 1A, and 1B may be omitted.

The image data to be image-processed by the image processing device 20 is not limited to image data collected by the ultrasonic diagnostic apparatuses 1, 1A and 1B, as long as they are luminance-displayable image data. Image data collected by other image diagnostic apparatuses such as an X-ray CT apparatus, MRI apparatus, and so forth can also be employed.

What is claimed is:

1. An ultrasonic diagnostic apparatus comprising:
    a unit configured to generate image data for displaying a tomogram of a subject by luminance according to signal intensities of echo signals obtained through ultrasonic waves transmitted to the subject;
    an image reconstructing unit configured to generate reconstructed images by alternating, on the basis of a degree of luminance levels, at least one of a luminance and a color of an area of a predetermined luminance so that the area of the predetermined luminance is emphasized in the image data while the predetermined luminance is altered in turn; and
    an image synthesizing unit configured to supply the reconstructed images to a display unit so that the reconstructed images are displayed on the display unit in turn.

2. An ultrasonic diagnostic apparatus comprising:
    a unit configured to generate image data for displaying a tomogram of a subject by luminance according to signal intensities of echo signals obtained through ultrasonic waves transmitted to the subject;

a luminance scale altering unit configured to generate new luminance scales by altering, on the basis of a degree of luminance levels, at least ones of colors and color tones corresponding to partial luminance levels of a luminance scale with which the image data are to be displayed by the luminance, the partial luminance levels being different from each other;

an image reconstructing unit configured to perform an image reconstruction processing to the image data according to the new luminance scales respectively to generate a plurality of new image data;

a coloring condition setting unit configured to set times for displaying the plurality of new image data as a display time information and an order for displaying the plurality of new image data, the order serving as display order information; and an image synthesizing unit configured to give the plurality of new image data to a display unit so that the plurality of new image data are displayed in a display order designated by the display order information during display times designated by the display time information on the display unit.

3. An ultrasonic diagnostic apparatus according to claim 2, wherein the image synthesizing unit is configured to give the image data generated by the unit for generating the image data to the display unit to be displayed in a rows.

4. An ultrasonic diagnostic apparatus according to claim 2, wherein the unit configured to generate the image data is further configured to generate three-dimensional data as the image data; and the image reconstructing unit is configured to perform the image reconstruction processing to two-dimensional image data obtained by two-dimensionally projecting the three-dimensional data.

5. An ultrasonic diagnostic apparatus comprising:

a unit configured to generate a plurality of image data in a time series for displaying tomograms of a subject by luminance according to signal intensities of echo signals obtained through ultrasonic waves transmitted to the subject at least two times, the tomograms corresponding to a plurality of frames;

an image generating unit configured to perform a maximum luminance level holding operation which is an operation for holding a luminance level at a corresponding position spatially of the plurality of image data to a maximum so as to generate a plurality of new image data;

a first color tone altering unit configured to perform an image reconstruction processing which alters, on the basis of a degree of luminance levels, a color tone of the plurality of new image data to a first predetermined color tone; a second color tone altering unit configured to perform another image reconstruction processing which alters, on the basis of a degree of luminance levels, a color tone of a plurality of image data in a time series without the maximum luminance level holding operation to a second predetermined color tone; and an image synthesizing unit configured to give image data having the first color tone altered and image data having the second color tone altered to a display unit so that they are super positioned to be displayed using mixed colors determined by the first color tone and the second color tone with time variation on the display unit.

6. An ultrasonic diagnostic apparatus according to claim 5, wherein the image synthesizing unit is configured to give the plurality of image data generated by the unit for generating the plurality of image data to the display unit to be displayed in rows.

7. An ultrasonic diagnostic apparatus according to claim 5, wherein the unit configured to generate the plurality of image data is further configured to generate a plurality of three-dimensional data as the plurality of image data;

the first color tone altering unit is configured to perform the image reconstruction processing to a plurality of two-dimensional image data obtained by two-dimensionally projecting a plurality of new three-dimensional data subjected generated on the maximum luminance level holding operation; and the second color tone altering unit is configured to perform the another image reconstruction processing to a plurality of two-dimensional image data obtained by two-dimensionally projecting the plurality of three-dimensional data generated with the unit for generating the plurality of image data.

8. An ultrasonic diagnostic apparatus according to claim 5, wherein the first color tone altering unit is configured to perform the image reconstruction processing using at least one tone of reference colors on a gray scale as the first color tone; and the second color tone altering unit is configured to perform the another image reconstruction processing using at least one remained tone of the reference colors as the second color tone.

9. An ultrasonic diagnostic apparatus according to claim 5, wherein the first color tone altering unit is configured to perform the image reconstruction processing using at least one tone of reference colors on a gray scale as the first color tone, the reference colors substantially consisting of a red color, a blue color and a green color; and the second color tone altering unit is configured to perform the another image reconstruction processing using at least one remained tone of the reference colors as the second color tone.

10. An ultrasonic diagnostic apparatus comprising:

a unit configured to generate a plurality of image data in a time series for displaying tomograms of a subject by luminance according to signal intensities of echo signals obtained through ultrasonic waves transmitted to the subject at least two times, the tomograms corresponding to a plurality of frames;

a timing setting unit configured to generate a time information according to an information designating a timing input from an input device;

a first color tone altering unit configured to perform an image reconstruction processing which alters, on the basis of a degree of luminance levels, a color tone of specific image data included in the plurality of image data to a first predetermined color tone, the specific image data corresponding on a time designated by the time information;

a second color tone altering unit configured to perform another image reconstruction processing which alters, on the basis of a degree of luminance levels, a color tone of at least two image data in a time series included in the plurality of image data to a second predetermined color tone, the two image data corresponding after the time designated by the time information; and an image synthesizing unit configured to give image data having the first color tone altered and image data having the second color tone altered to a display unit so that they are superpositioned to be displayed using mixed colors determined by the first color tone and the second color tone with time variation on the display unit.

11. An ultrasonic diagnostic apparatus according to claim 10, wherein the image synthesizing unit is configured to give the plurality of image data generated by the unit for generating the plurality of image data to the display unit to be displayed in rows.

12. An ultrasonic diagnostic apparatus according to claim 10, wherein the unit configured to generate the plurality of image data is further configured to generate a plurality of three-dimensional data as the plurality of image data;
the first color tone altering unit is configured to perform the image reconstruction processing to specific two-dimensional image data of a plurality of two-dimensional image data obtained by two-dimensionally projecting the plurality of three-dimensional data; and
the second color tone altering unit is configured to perform the another image reconstruction processing to at least two of the plurality of two-dimensional image data, the two of the plurality of two-dimensional image data each corresponding to a time after the time designated by the time information.

13. An ultrasonic diagnostic apparatus according to claim 10,
wherein the first color tone altering unit is configured to perform the image reconstruction processing using at least one tone of reference colors on a gray scale as the first color tone; and
the second color tone altering unit is configured to perform the another image reconstruction processing using at least one remained tone of the reference colors as the second color tone.

14. An ultrasonic diagnostic apparatus according to claim 10,
wherein the first color tone altering unit is configured to perform the image reconstruction processing using at least one tone of reference colors on a gray scale as the first color tone, the reference colors substantially consisting of a red color, a blue color and a green color; and
the second color tone altering unit is configured to perform the another image reconstruction processing using at least one remained tone of the reference colors as the second color tone.

15. An ultrasonic diagnostic apparatus comprising:
a unit configured to generate image data for displaying a tomogram of a subject by luminance according to signal intensities of echo signals obtained through ultrasonic waves transmitted to the subject;
a luminance scale altering unit configured to generate new luminance scale repeatedly by altering, on the basis of a degree of luminance levels, at least ones of colors and color tones corresponding to partial luminance levels of a background color in a luminance scale with which the image data are to be displayed by the luminance to at least ones of other colors and other color tones reducing an influence of an optical illusion;
an image reconstructing unit configured to sequentially perform an image reconstruction processing to the image data according to the repeatedly generated new luminance scale to generate new image data repeatedly; and
an image synthesizing unit configured to give the new image data to a display unit so that the repeatedly generated new image data are to be displayed sequentially on the display unit.

16. An ultrasonic diagnostic apparatus according to claim 15,
wherein the image synthesizing unit is configured to give the image data generated by the unit for generating the image data to the display unit to be displayed in rows.

17. An ultrasonic diagnostic apparatus according to claim 15, wherein the unit configured to generate the image data is further configured to generate three-dimensional data as the image data; and
the image reconstructing unit is configured to perform the image reconstruction processing to two-dimensional image data obtained by two-dimensionally projecting the three-dimensional data.

18. An image processing apparatus comprising:
an image reconstructing unit configured to generate reconstructed images by alternating, on the basis of a degree of luminance levels, at least one of a luminance and a color of an area of a predetermined luminance in image data generated for displaying a tomogram of a subject by luminance so that the area of the predetermined luminance is emphasized in the image data while the predetermined luminance is altered in turn; and
an image synthesizing unit for supplying the reconstructed images to a display unit so that the reconstructed images are displayed on the display unit in turn.

19. An image processing apparatus comprising:
a luminance scale altering unit configured to generate new luminance scales by altering, on the basis of a degree of luminance levels, at least ones of colors and color tones corresponding to partial luminance levels of a luminance scale with which image generated for displaying a tomogram of a subject by luminance data are to be displayed by the luminance, the partial luminance levels being different each other;
an image reconstructing unit configured to perform an image reconstruction processing to the image data according to the new luminance scales respectively to generate a plurality of new image data; and
a coloring condition setting unit for setting times for displaying the plurality of new image data as a display time information and an order for displaying the plurality of new image data the order serving as display order information.

20. An image processing apparatus comprising:
an image generating unit configured to perform a maximum luminance level holding operation which is an operation for holding a luminance level at a corresponding position spatially of plurality of image data generated in a time series for displaying tomograms of a subject by luminance to a maximum so as to generate a plurality of new image data, the tomograms corresponding to a plurality of frames;
a first color tone altering unit configured to perform an image reconstruction processing which alters, on the basis of a degree of luminance levels, a color tone of the plurality of new image data to a first predetermined color tone;
a second color tone altering unit configured to perform another image reconstruction processing which alters, on the basis of a degree of the luminance levels, a color tone of a plurality of image data in a time series without the maximum luminance level holding operation to a second predetermined color tone; and
an image synthesizing unit configured to give image data having the first color tone altered and image data having the second color tone altered to a display unit so that they are super positioned to be displayed using mixed colors determined by the first color tone and the second color tone with time variation on the display unit.

21. An image processing apparatus comprising:

a timing setting unit configured to generate a time information according to an information designating a timing input from an input device;

a first color tone altering unit configured to perform an image reconstruction processing which alters, on the basis of a degree of luminance levels, a color tone of specific image data included in a plurality of image data generated in a time series for displaying tomograms corresponding to frames of a subject by luminance to a first predetermined color tone, the specific image data corresponding on a time designated by the time information;

a second color tone altering unit configured to perform another image reconstruction processing which alters, on the basis of a degree of luminance levels, a color tone of at least two image data in a time series included in the plurality of image data to a predetermined second color tone, the two image data corresponding after the time designated by the time information; and an image synthesizing unit configured to give image data having the first color tone altered and image data having the second color tone altered to a display unit so that they are superpositioned to be displayed using mixed colors determined by the first color tone and the second color tone with time variation on the display unit.

22. An image processing apparatus comprising:

a luminance scale altering unit configured to generate new luminance scale repeatedly by altering, on the basis of a degree of luminance levels, at least ones of colors and color tones corresponding to partial luminance levels of a background color in a luminance scale with which image data generated for displaying a tomogram of a subject by luminance are to be displayed by the luminance to at least ones of other colors and other color tones reducing an influence of an optical illusion; and an image reconstructing unit configured to sequentially perform an image reconstruction processing to the image data according to the repeatedly generated new luminance scale to generate new image data repeatedly.

* * * * *